(12) United States Patent
Miyake et al.

(10) Patent No.: US 11,548,975 B2
(45) Date of Patent: Jan. 10, 2023

(54) ISOCYANATE COMPOSITION AND METHOD FOR PRODUCING ISOCYANATE POLYMER

(71) Applicant: ASAHI KASEI KABUSHIKI KAISHA, Tokyo (JP)

(72) Inventors: Nobuhisa Miyake, Tokyo (JP); Masaaki Shinohata, Tokyo (JP); Atsushi Ohkubo, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 527 days.

(21) Appl. No.: 16/340,994

(22) PCT Filed: Oct. 13, 2017

(86) PCT No.: PCT/JP2017/037275
§ 371 (c)(1),
(2) Date: Apr. 10, 2019

(87) PCT Pub. No.: WO2018/070539
PCT Pub. Date: Apr. 19, 2018

(65) Prior Publication Data
US 2019/0225739 A1 Jul. 25, 2019

(30) Foreign Application Priority Data

Oct. 14, 2016 (JP) .............................. JP2016-203092
Oct. 14, 2016 (JP) .............................. JP2016-203098

(51) Int. Cl.
| | | |
|---|---|---|
| *C08G 18/72* | (2006.01) | |
| *C08K 3/32* | (2006.01) | |
| *C08K 3/30* | (2006.01) | |
| *C08K 5/521* | (2006.01) | |
| *C08K 5/41* | (2006.01) | |
| *C08G 18/73* | (2006.01) | |
| *C07C 263/10* | (2006.01) | |
| *C08G 18/02* | (2006.01) | |
| *C09D 175/06* | (2006.01) | |
| *C08K 5/109* | (2006.01) | |
| *C08K 5/12* | (2006.01) | |
| *C08K 5/205* | (2006.01) | |
| *C08G 18/75* | (2006.01) | |
| *C08K 5/00* | (2006.01) | |
| *C08G 18/76* | (2006.01) | |

(52) U.S. Cl.
CPC ............ *C08G 18/72* (2013.01); *C07C 263/10* (2013.01); *C08G 18/022* (2013.01); *C08G 18/73* (2013.01); *C08G 18/735* (2013.01); *C08G 18/758* (2013.01); *C08G 18/7614* (2013.01); *C08K 3/30* (2013.01); *C08K 3/32* (2013.01); *C08K 5/005* (2013.01); *C08K 5/109* (2013.01); *C08K 5/12* (2013.01); *C08K 5/205* (2013.01); *C08K 5/41* (2013.01); *C08K 5/521* (2013.01); *C09D 175/06* (2013.01); *C08K 2003/309* (2013.01); *C08K 2003/329* (2013.01)

(58) Field of Classification Search
CPC ...... C08G 18/72; C08G 18/022; C08G 18/73; C08G 18/735; C08G 18/758; C08G 18/7614; C07C 263/10; C08K 3/30; C08K 3/32; C08K 5/005; C08K 5/109; C08K 5/12; C08K 5/205; C08K 5/41; C08K 5/521; C08K 2003/309; C08K 2003/329; C09D 175/06
See application file for complete search history.

(56) References Cited

U.S. PATENT DOCUMENTS

| | | | |
|---|---|---|---|
| 3,247,236 | A | 4/1966 | Adams |
| 3,976,622 | A | 8/1976 | Wagner et al. |
| 4,064,157 | A | 12/1977 | Nafziger et al. |
| 4,176,132 | A | 11/1979 | Ide et al. |
| 4,290,969 | A | 9/1981 | Komatsu et al. |
| 4,318,861 | A | 3/1982 | Babiec, Jr. et al. |
| 4,324,879 | A | 4/1982 | Bock et al. |
| 4,412,073 | A | 10/1983 | Robin |
| 4,837,359 | A | 6/1989 | Woynar et al. |
| 4,983,762 | A | 1/1991 | Robin |
| 5,175,349 | A | 12/1992 | Gupta et al. |
| 5,641,851 | A | 6/1997 | Wolff et al. |
| 5,728,317 | A | 3/1998 | Laqua et al. |
| 6,392,001 | B1 | 5/2002 | Mertes et al. |

(Continued)

FOREIGN PATENT DOCUMENTS

| | | |
|---|---|---|
| CA | 2130685 A1 | 3/1995 |
| CA | 2 325 034 A1 | 9/1999 |

(Continued)

OTHER PUBLICATIONS

International Search Report issued in corresponding International Patent Application No. PCT/JP/037275, dated Jan. 16, 2018.
Written Opinion issued in corresponding International Patent Application No. PCT/JP2017/037275, dated Jan. 16, 2018.
European Search Repod in corresponding European Application No. 17859947.8 dated Sep. 18, 2019 in English.
Office Action issued in related U.S. Appl. No. 16/340,532 dated Oct. 23, 2020.
European Search Report dated Oct. 2, 2019 issued in corresponding European Patent Application No. 17859611.0.

(Continued)

*Primary Examiner* — Rabon A Sergent
(74) *Attorney, Agent, or Firm* — Morgan, Lewis & Bockius LLP

(57) ABSTRACT

An isocyanate composition according to the present invention contains: a difunctional or more-functional isocyanate compound; and 1.0 ppm by mass to $1.0 \times 10^4$ ppm by mass, based on the isocyanate compound, of a compound having at least one unsaturated bond excluding unsaturated bonds constituting an aromatic ring, the compound being different from the isocyanate.

6 Claims, 1 Drawing Sheet

(56) References Cited

U.S. PATENT DOCUMENTS

| | | | |
|---|---|---|---|
| 11,174,337 B2 * | 11/2021 | Miyake | C08G 18/8116 |
| 2004/0049003 A1 | 3/2004 | Asahina et al. | |
| 2007/0197759 A1 | 8/2007 | Binder et al. | |
| 2013/0338330 A1 | 12/2013 | Nakagawa et al. | |
| 2015/0210631 A1 | 7/2015 | Shinohata et al. | |
| 2019/0225739 A1 | 7/2019 | Miyake et al. | |
| 2020/0048403 A1 * | 2/2020 | Miyake | C08K 5/098 |

FOREIGN PATENT DOCUMENTS

| | | | | |
|---|---|---|---|---|
| CA | 2325034 A1 * | 9/1999 | | C07C 263/18 |
| CN | 1478112 A | 2/2004 | | |
| CN | 104250363 A | 12/2014 | | |
| EP | 0 561 568 A1 | 9/1993 | | |
| EP | 0 744 422 A1 | 11/1996 | | |
| EP | 2915803 A1 | 9/2015 | | |
| GB | 994890 A | 6/1965 | | |
| GB | 2 031 914 A | 4/1980 | | |
| JP | 46-035246 B | 10/1971 | | |
| JP | 53-135931 A | 11/1978 | | |
| JP | 56-061341 A | 5/1981 | | |
| JP | 57-047319 A | 3/1982 | | |
| JP | 57-115416 A | 7/1982 | | |
| JP | 60-054349 B | 11/1985 | | |
| JP | 63-057577 A | 3/1988 | | |
| JP | 04-066863 B | 10/1992 | | |
| JP | 05-255469 A | 10/1993 | | |
| JP | 06-092925 A | 4/1994 | | |
| JP | 07-149705 A | 6/1995 | | |
| JP | 07-304724 A | 11/1995 | | |
| JP | 2002-003462 A | 1/2002 | | |
| JP | 2002-003568 A | 1/2002 | | |
| JP | 2002-507594 A | 3/2002 | | |
| JP | 2002-363151 A | 12/2002 | | |
| JP | 2005-047854 A | 2/2005 | | |
| JP | 2005-048073 A | 2/2005 | | |
| JP | 2007-528885 A | 10/2007 | | |
| JP | 2008-143872 A | 6/2008 | | |
| JP | 2015-010183 A | 1/2015 | | |
| JP | 2015-501358 A | 1/2015 | | |
| JP | 2015-028163 A | 2/2015 | | |
| JP | 5849088 B2 | 1/2016 | | |
| JP | 2016-069496 A | 5/2016 | | |
| JP | 2017-031174 A | 2/2017 | | |
| WO | 02/42351 A1 | 5/2002 | | |
| WO | 2004/078819 A1 | 9/2004 | | |
| WO | 2012/121291 A1 | 9/2012 | | |
| WO | 2013060614 A1 | 5/2013 | | |
| WO | 2014/069605 A1 | 5/2014 | | |

OTHER PUBLICATIONS

Written Opinion of the International Search Authority dated Jan. 9, 2018, issued in corresponding application PCT/JP2017/037276.
International Search Report issued in corresponding application PCT/JP2017/037276 dated Jan. 9, 2018.
International Search Report issued in corresponding International Patent Application No. PCT/JP2017/037275, dated Jan. 16, 2018.
Gui et al., "New Polyurethane Resin Coating Production Technology and Application," Guangdong Science and Technology Press, 1st Edition, pp. 75-76 (2001). See Chinese Office Action.
Office Action issued in corresponding Chinese Application No. 201780062137.1 dated Jul. 8, 2021.

* cited by examiner

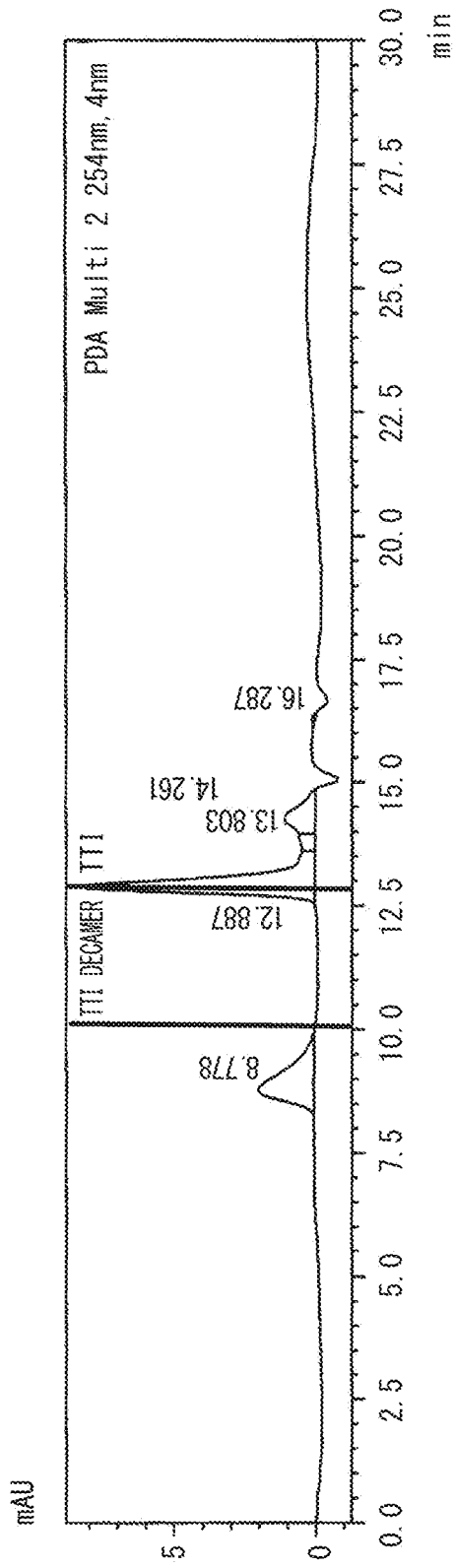

ISOCYANATE COMPOSITION AND METHOD FOR PRODUCING ISOCYANATE POLYMER

TECHNICAL FIELD

The present invention relates to an isocyanate composition and a method for producing an isocyanate polymer.

The present invention claims priority on the basis of Japanese Patent Application No. 2016-203092 and Japanese Patent Application No. 2016-203098 filed in Japan on Oct. 14, 2016, the contents of which are incorporated herein by reference.

BACKGROUND OF THE INVENTION

A polyurethane having a urethane bond is mainly prepared by reaction of a difunctional or more-functional isocyanate and a difunctional or more-functional alcohol, is a polymer excellent in tensile strength, abrasion resistance and oil resistance, and is used in a wide number of materials including soft foams, hard foams, elastomers, adhesive agents, coating materials, and binders. Among these, a polyurethane obtained using a chain or cyclic aliphatic isocyanate as a raw material is excellent in weather resistance and light resistance, and is used in areas where external appearance is importance, such as in baking coatings, automobile clear coating materials, coil coating materials, and the like.

Although diisocyantes, which are difunctional isocyanates, are often used as isocyanates, the dissociates are often polymerized by reaction of the following formulae (a) to (c) to be used as isocyanate polymers so as to improve physical properties of polyurethane and limit the vapor pressure to ensure the safety of operators.

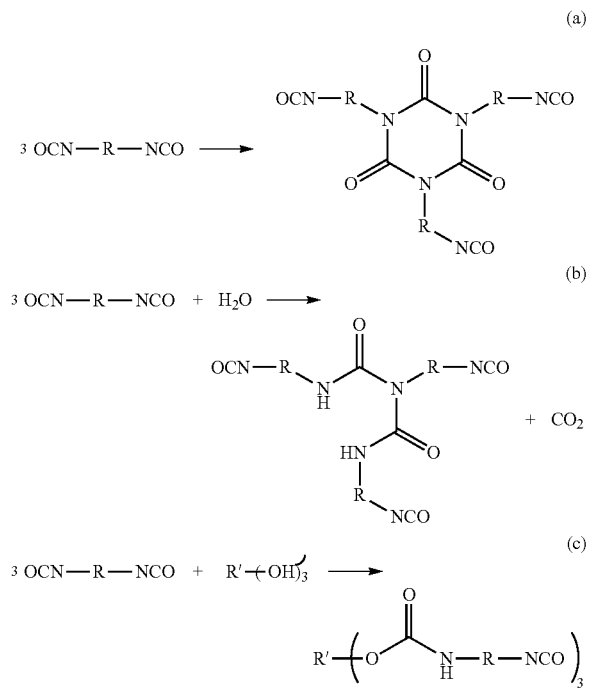

In the formulae (a) to (c), R represents a divalent organic group, and R' represents a trivalent organic group.

An isocyanurate-type isocyanate polymer is obtained in the reaction of the formula (a), a biuret-type isocyanate polymer is obtained in the reaction of the formula (b), and a urethane isocyanate polymer is obtained in the reaction of the formula (c).

The biuret-type isocyanate polymer is described in Patent Documents 1 to 6. The isocyanurate-type isocyanate polymer is described in Patent Documents 7 to 10. An allophanate-type isocyanate polymer is described in Patent Documents 11 and 12.

On the other hand, there is an example of an isocyanate having a trifunctional or more-functional isocyanate group (see, for example, Patent Document 13). The trifunctional or more-functional isocyanate is advantageous in terms that the trifunctional or more-functional isocyanate does not need polymerization of diisocyanates required for suppressing the vapor pressure of the difunctional diisocyanate, because the vapor pressure of the trifunctional or more-functional isocyanate is low. Furthermore, although a liner chain polyurethane is obtained by reacting a difunctional diisocyanate with a diol, a polyurethane having a cross-linked structure is obtained by reacting a trifunctional or more-functional isocyanate with a diol, and exhibits effects of improving physical properties or external appearance of a coating film, when used as a coating material, for example.

Thus, it is known that a trifunctional or more-functional isocyanate is advantageous in comparison with a diisocyanate.

DOCUMENTS OF RELATED ART

Patent Documents

Patent Document 1: U.S. Pat. No. 3,976,622
Patent Document 2: U.S. Pat. No. 4,176,132
Patent Document 3: U.S. Pat. No. 4,290,969
Patent Document 4: U.S. Pat. No. 4,837,359
Patent Document 5: U.S. Pat. No. 4,983,762
Patent Document 6: U.S. Pat. No. 5,641,851
Patent Document 7: U.S. Pat. No. 4,324,879
Patent Document 8: U.S. Pat. No. 4,412,073
Patent Document 9: Japanese Unexamined Patent Application Publication No. Sho 57-47319
Patent Document 10: Japanese Unexamined Patent Application Publication No. Sho 63-57577
Patent Document 11: English Patent No. 994890
Patent Document 12: Japanese Unexamined Patent Application Publication No. Hei 7-304724
Patent Document 13: Japanese Unexamined Patent Application Publication No. Sho 56-61341

SUMMARY OF THE INVENTION

Problems to be Solved by the Invention

However, a trifunctional or more-functional isocyanate has a structure that causes cross-linking, and therefore the viscosity of an isocyanate composition tends to increase or the isocyanate composition tends to generate gelatinous components when stored. There is a case where uneven coating occurs, the coating film performance is deteriorated, or beauty appearance is deteriorated by using an isocyanate having an increased viscosity or generated gelatinous components, as a coating raw material. In addition, there is a case where the incorporation of a small amount of moisture into a difunctional diisocyanate forms a biuret bond shown in the right portion of the formula (b) to generate a trifunctional isocyanate, and the resultant trifunctional isocyanate causes cross-linking to increase the viscosity or generate gelatinous components in an isocyanate composition when stored in the same way as that of the trifunctional or more-functional isocyanate. Although a difunctional isocyanate exhibits less tendency than the trifunctional or more-functional, the difunctional isocyanate may cause uneven coating, deteriorate the coating film performance or the beauty appearance, when used as a coating raw material.

In view of the above-mentioned circumstances, the present invention aims to provide an isocyanate composition containing a difunctional diisocyanate and/or a trifunctional or more-functional isocyanate, the isocyanate composition being excellent in the storage stability. In addition, the present invention aims to provide a method for producing an isocyanate polymer by polymerizing the isocyanate composition.

Means to Solve the Problems

The present inventors have made intensive studies in order to solve the above problems, found that an isocyanate composition containing specific components achieves the above-mentioned problems, and the use of the isocyanate composition makes it possible to produce an isocyanate polymer in which coloration is sufficiently suppressed, and thereby completed the present invention.

The present invention encompasses the following aspects.
(1) An isocyanate composition containing:
 a trifunctional or more-functional isocyanate compound; and
 a compound having at least one unsaturated bond excluding unsaturated bonds constituting an aromatic ring, the compound being different from the isocyanate, in an amount of 1.0 ppm by mass to $1.0 \times 10^4$ ppm by mass, based on the isocyanate compound.
(2) The isocyanate composition according to (1), wherein the compound having at least one unsaturated bond is a compound having an UV absorption in an area of decamer or higher isocyanates in a measurement spectrum of gel permeation chromatography.
(3) The isocyanate composition according to (1), wherein the compound having at least one unsaturated bond is a compound of formula (1).

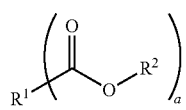

(1)

In the formula, $R^1$ represents a C2-10 aliphatic group or a C6-10 aromatic group, which may have an isocyanate group, $R^2$ represents a C2-10 aliphatic group or a C2-25 aromatic group, which does not have an isocyanate group, and a represents an integer of 1 or 2.
(4) The isocyanate composition according to (1), wherein the compound having at least one unsaturated bond is a compound having an isocyanurate group and/or a biuret group.
(5) The isocyanate composition according to any one of (1) to (4), further containing, based on the isocyanate compound, 1.0 ppm by mass to $1.0 \times 10^4$ ppm by mass of at least one inert compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound having neither an unsaturated bond between carbon atoms nor a double bond between a carbon atom and an oxygen atom, excluding unsaturated bonds constituting an aromatic ring; and/or,
 1.0 ppm by mass to $1.0 \times 10^3$ ppm by mass of a sulfuric acid and/or a sulfuric acid ester; and/or,
 1.0 ppm by mass to $1.0 \times 10^3$ ppm by mass of a phosphoric acid and/or a phosphoric acid ester.
(6) The isocyanate composition according to any one of (1) to (5), further containing: 1.0 ppm by mass to $1.0 \times 10^2$ ppm by mass, based on the isocyanate compound, of a halogen atom which is not derived from a halogenated hydrocarbon compound.
(7) The isocyanate composition according to any one of (1) to (6), wherein the amount of the isocyanate compound is 97% by mass or more, based on the total of the isocyanate composition.
(8) An isocyanate composition containing:
 a trifunctional or more-functional isocyanate compound;
 1.0 ppm by mass to $1.0 \times 10^3$ ppm by mass, based on the isocyanate compound, of a sulfuric acid and/or a sulfuric acid ester; and/or
 1.0 ppm by mass to $1.0 \times 10^3$ ppm by mass, based on the isocyanate compound, of a phosphoric acid and/or a phosphoric acid ester.
(9) An isocyanate composition containing:
 a difunctional or more-functional isocyanate compound;
 1.0 ppm by mass to $1.0 \times 10^4$ ppm by mass, based on the isocyanate compound, of a compound having an UV absorption in an area of decamer or higher isocyanates in a measurement spectrum of gel permeation chromatography; and/or,
 1.0 ppm by mass to $1.0 \times 10^4$ ppm by mass, based on the isocyanate compound, of a compound having an isocyanurate group and/or a biuret group.
(10) The isocyanate composition according to (9), containing, based on the isocyanate compound, 1.0 ppm by mass to $1.0 \times 10^3$ ppm by mass of a sulfuric acid and/or a sulfuric acid ester, and/or, 1.0 ppm by mass to $1.0 \times 10^3$ ppm by mass of a phosphoric acid and/or a phosphoric acid ester.
(11) A method for producing an isocyanate polymer, containing reacting an isocyanate compound contained in the isocyanate composition of any one of (1) to (10) described above,
 wherein the isocyanate polymer contains: a unit of formula (A) or (B); and at least one unit selected from the group consisting of units of formulae (2), (3), (4), (5), (6), (7) and (8), and
 a nitrogen atom constituting the isocyanate polymer bonds with a carbon atom.

 (A)

 (B)

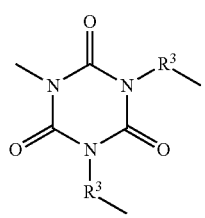 (2)

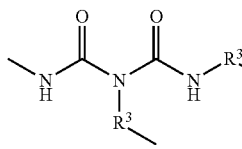 (3)

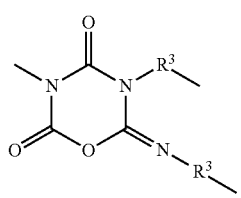 (4)

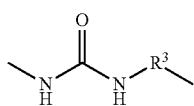 (5)

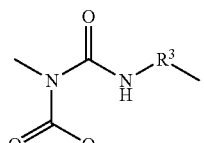 (6)

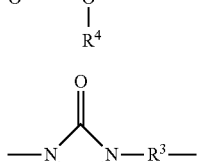 (7)

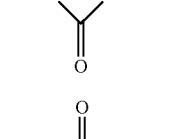 (8)

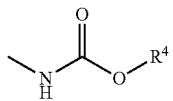

In the formulae, each $R^3$ independently represents a residual group obtained by removing two isocyanate groups from the isocyanate compound, and each $R^4$ independently represents a monovalent organic group.

Effects of the Invention

The present invention provides an isocyanate composition containing a difunctional diisocyanate and/or a trifunctional or more-functional isocyanate, the storage stability of which is improved. In addition, the present invention provides a method for producing a polyisocyanate composition by polymerizing the isocyanate composition.

BRIEF DESCRIPTION OF DRAWINGS

FIG. 1 is a drawing showing a measurement spectrum of gel permeation chromatography obtained in Synthesis Example B3.

EMBODIMENTS FOR CARRYING OUT THE INVENTION

Preferable embodiments of the present invention will be described below. The present invention is not limited to the following embodiments, and the present invention may be modified in various ways within the summary thereof.

The present invention provides in an embodiment an isocyanate composition containing: a difunctional or more-functional isocyanate compound; and 1.0 ppm by mass to $1.0 \times 10^4$ ppm by mass, based on the isocyanate compound, of a compound having at least one unsaturated bond excluding unsaturated bonds constituting an aromatic ring, the compound being different from the isocyanate, or 1.0 ppm by mass to $1.0 \times 10^3$ ppm by mass, based on the isocyanate compound, of a sulfuric acid and/or a sulfuric acid ester, and/or, 1.0 ppm by mass to $1.0 \times 10^3$ ppm by mass, based on the isocyanate compound, of a phosphoric acid and/or a phosphoric acid ester.

The isocyanate compound is preferably contained in an amount of 97% by mass or more, relative to the total mass of the isocyanate composition.

The isocyanate composition according to the present embodiment is excellent in the storage stability in spite of the presence of a difunctional or more-functional isocyanate. In the present specification, the phrase "an isocyanate composition is excellent in the storage stability" means that even when the isocyanate composition is stored for a long time, the viscosity increase, the generation of gelatinous components, or the chromaticity increase is suppressed in the composition. The phrase "stored for a long time" means storage is conducted, for example, for 100 days or more, 200 days or more, 300 days or more, or 500 days or more.

Thus, the isocyanate composition according to the present embodiment is also referred to as "an isocyanate composition to be stored for a long time". Alternatively or, the compound having at least one unsaturated bond excluding unsaturated bonds constituting an aromatic ring, or, the sulfuric acid, the sulfuric acid ester, the phosphoric acid, and/or the phosphoric acid ester may be also referred to as a quality improving agent, a stabilizer, a viscosity increase inhibitor, a gelatinous component generation inhibitor, or a chromaticity increase inhibitor, of a difunctional diisocyanate and/or a trifunctional or more-functional isocyanate compound.

Hereinafter, compounds contained in the isocyanate composition according to the present embodiment will be explained.

<Difunctional or More-Functional Isocyanate Compound>

In the isocyanate composition according to the present embodiment, a compound of the following formula (10) is preferably used as a difunctional or more-functional isocyanate compound.

$$R^{33}\!-\!\!\text{\Large(}NCO\text{\Large)}_c \qquad (10)$$

In the formula (10), c represents an integer of 2 or more, and $R^{33}$ represents an organic group with a valence of c.

In the formula (10), $R^{33}$ preferably represents a C3-85 organic group, and more preferably a C3-30 organic group.

$R^{33}$ represents an aliphatic group, an aromatic group, or a group formed by bonding an aliphatic group and an aromatic group. Specific examples of $R^{33}$ include cyclic groups such as cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, side chain-containing cyclic hydrocarbon groups), heterocyclic groups, heterocyclic spiro groups, and hetero cross-linked cyclic groups; acyclic hydrocarbon groups, groups in which an acyclic hydrocarbon group and at least one cyclic group are bonded, and groups in which the above-mentioned groups are bonded with specific nonmetallic atoms (such as carbon, oxygen, nitrogen, sulfur, or silicon) via covalent bonds.

The phrase "bonded with specific nonmetallic atoms via covalent bonds" means the state in which, for example, the above-mentioned group is bonded with any of groups of the following formulae (11) to (23) via a covalent bond.

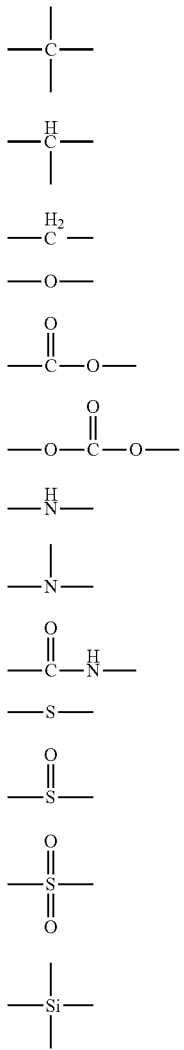

In the isocyanate composition according to the present embodiment, the isocyanate compound is preferably a compound of formula (10) in which c represents an integer of 2 to 5, more preferably 2 or 3, and even more preferably 3, in view of the easiness of preparation or handling. Among the bonds of the formulae (11) to (23), an isocyanate compound having a bond of formula (11) to (16), (18), (20), or (23) is preferable, and an isocyanate compound having a bond of formula (12) or (18) is more preferable.

As a difunctional diisocyanate compound of the formula (10) in which c represents 2, a C4-30 aliphatic diisocyanate, a C8-30 alicyclic diisocyanate, or a C8-30 aromatic group-containing diisocyanate is preferably used, for example.

Specific examples of the C4-30 aliphatic diisocyanate include 1,4-tetramethylene diisocyanate, 1,5-pentamethylene diisocyanate, 1,4-diisocyanato-2-methylbutane, 1,6-hexamethylene diisocyanate, 1,6-diisocyanato-2,5-dimethylhexane, 2,2,4-trimethyl-1,6-hexamethylene diisocyanate, lysine methyl ester diisocyanate, and lysine ethyl ester diisocyanate.

Specific examples of the C8-30 alicyclic diisocyanate include isophorone diisocyanate, 1,3-bis(isocyanate methyl)-cyclohexane, 4,4'-dicyclohexylmethane diisocyanate, hydrogenated tetramethylxylylene diisocyanate, and norbornene diisocyanate.

Examples of the C8-30 aromatic group-containing diisocyanate include: 4,4'-diphenylmethane diisocyanate, 2,6-tolylene diisocyanate, xylylene diisocyanate, tetramethylxylylene diisocyanate, and naphthalene diisocyanate.

In the case where the compound has structural isomers, the structural isomers are encompassed in the above-mentioned examples.

In addition, compounds formed by dimerization of two molecules of the difunctional isocyanate via a urea bond or an uretdione structure may be used as a difunctional isocyanate.

An isocyanate compound of formula (24) is preferably used as a trifunctional isocyanate.

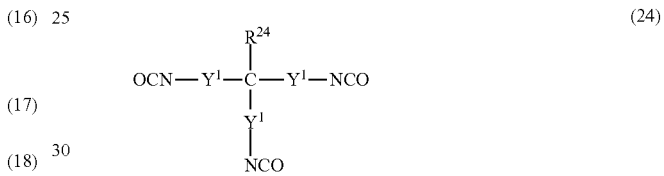

In the formula (24), a plurality of $Y^1$ each independently represent a single bond, or a C1-20 divalent hydrocarbon group which may contain an ester structure and/or an ether structure, and $R^{24}$ represents a hydrogen atom or a C1-12 monovalent hydrocarbon group.

In the formula (24), $R^{24}$ preferably represents a C1-10 aliphatic group or a C6-10 aromatic group, and specific examples thereof include: aliphatic groups, such as a methyl group, an ethyl group, a propyl group, a butyl group, a pentyl group, a hexyl group, and a decyl group; and aromatic groups such as a phenyl group, a methylphenyl group, an ethylphenyl group, a butylphenyl group, a dimethylphenyl group, and a diethylphenyl group.

In the formula (24), $Y^1$ preferably represents a C1-100 divalent aliphatic group, a C6-100 divalent aromatic group, a C2-100 divalent group in which aliphatic groups are bonded via an ester structure, a C2-100 divalent group in which aliphatic groups are bonded via an ether structure, a C7-100 divalent group in which an aliphatic group and an aromatic group are bonded via an ester structure, a C7-100 divalent group in which an aliphatic group and an aromatic group are bonded via an ether structure, a C14-100 divalent group in which aromatic groups are bonded via an ester structure, or a C14-100 divalent group in which aromatic groups are bonded via an ether structure.

Further specific examples of the isocyanate compound of the formula (24) include: compounds in which $Y^1$ in the formula (24) represents a C1-100 divalent aliphatic group or a C6-100 divalent aromatic group, and compounds of the following formula (25), (26), or (27), and the compound of formula (25) or (27) is more preferable. Examples of the compounds in which $Y^1$ in the formula (24) is a C1-100 divalent aliphatic group or a C6-100 divalent aromatic group include 1,8-diisocyanate-4-isocyanate methyloctane, 1,3,6-triisocyanate hexane, 1,8-diisocyanato-4-(isocyanatomethyl)-2,4,7-trimethyloctane, 1,5-diisocyanato-3-(isocyanatomethyl)pentane, 1,6,11-triisocyanatoundecane, 1,4,7-triisocyanatoheptane, 1,2,2-triisocyanatobutane, 1,2,6-triisocyanatohexane, 1-isocyanato-2,2-bis(isocyanatomethyl)butane, 1,3,5-triisocyanatocyclohexane, 1,7-diisocyanato-4-(3-isocyanatopropyl)heptane, 1,3-diisocyanato-2-(isocyanatomethyl)-2-methylpropane, 1,3,5-triisocyanatobenzene, 1,3,5-triisocyanato-2-methylbenzene, 1,3,5-tris(1-isocyanatopropane-2-yl)benzene, 1,3,5-tris(1-isocyanatopropane-2-yl)-2-methylbenzene, 1,3,5-tris(1-isocyanatomethyl)-2-methylbenzene, and 2,2'-((2-isocyanato-1,3-phenylene)bis(methylene))bis(isocyanatebenzene).

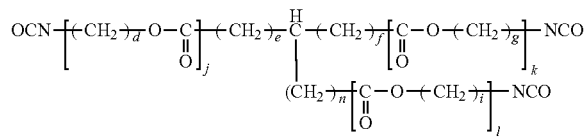

(25)

In the formula (25), d, g, and i each independently represent an integer of 1 to 4, e, f, and h each independently represent an integer of 0 to 5, and j, k, and l each independently represent 0 or 1.

Specific examples of the compound of the formula (25) include: 1,2,3-propane triisocyanate, wherein j, k and l represent 0, e and f represent 1, and h represents 0; tris(2-isocyanatoethyl)amine, wherein j, k, and l represent 0, e, f, and h represent 2; 1,6,11-triisocyanatoundecane, wherein j, k, and l represent 0, e and f represent 5, and h represents 0; 1,3,6-hexamethylene triisocyanate, wherein j, k, and l represent 0, e represents 3, f represents 2, and h represents 0; 1,8-diisocyanato-4-(isocyanatomethyl)octane, wherein j, k, and l represent 0, e represents 4, f represents 1, and h represents 3; 2-isocyanatoethyl-2,5-diisocyanatopentanoate, wherein e represents 3, f and h represent 0, j and l represent 0, and k represents 1; 2-isocyanatoethyl-2,6-diisocyanatohexanoate, wherein e represents 4, f and h represent 0, g represents 2, j and l represent 0, and k represents 1; bis(2-isocyanatoethyl)-2-isocyanatobutanedioate, wherein d and g represent 2, e represents 1, f and h represent 0, j and k represents 1, and l represent 0; bis(2-isocyanatoethyl)-2-isocyanatopentanedioate, wherein d and g represent 2, e represents 2, f and h represent 0, j and k represent 1, and l represents 0; and tris(2-isocyanatoethyl)hexane-1,3,6-tricarboxylate, wherein d, g, and i represent 2, j, k and l represent 1, e represent 3, f represents 2, and h represents 0.

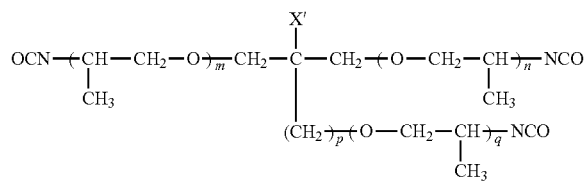

(26)

In the formula (26), X' represents a C1-4 hydrocarbon group, m, n and q each represent an integer of 1 or more, the sum of m, n, and q is 3 to 99, and p represents an integer of 0 to 3.

A compound of the following formula (27) is preferably used, and a compound of the following formula (27-1) is more preferably used, as an isocyanate compound in the isocyanate composition according to the present embodiment.

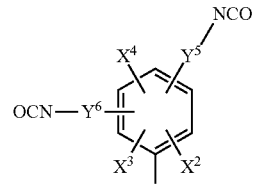

(27)

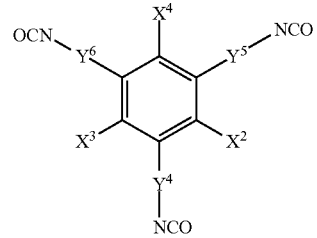

(27-1)

In the formulae (27) and (27-1), $X^2$ to $X^4$ each independently represent a hydrogen atom or a C1-12 monovalent hydrocarbon group, $Y^4$ to $Y^6$ each independently represent a C1-20 divalent hydrocarbon group which may have an ester structure and/or an ether structure, or a single bond.

In the formulae (27) and (27-1), $X^2$ to $X^4$ preferably represent a group defined as $R^{24}$ in the formula (24), and $Y^4$ to $Y^6$ preferably represent a single bond, a C1-20 divalent aliphatic group, a C6-20 divalent aromatic group, a C2-20 divalent group in which aliphatic groups are bonded via an ester structure, a C2-20 divalent group in which aliphatic groups are bonded via an ether structure, a C7-20 divalent group in which an aliphatic group and an aromatic group are bonded via an ester structure, a C7-20 divalent group in which an aliphatic group and an aromatic group are bonded via an ether structure, a C14-20 divalent group in which aromatic groups are bonded via an ester structure, or a C14-20 divalent group in which aromatic groups are bonded via an ether structure, and more preferably represents a single bond, a C1-20 divalent aliphatic group, or a C6-20 divalent aromatic group. Among these, $X^2$ to $X^4$ more preferably represent a hydrogen atom or a C1-6 alkyl group, and $Y^4$ to $Y^6$ more preferably represent a single bond, or a C1-6 alkylene group.

In addition, a compound in which three molecules of the difunctional isocyanate are trimerized via an isocyanurate ring structure or a biuret bond may be used as a trifunctional isocyanate.

Specific examples of the compound of the formula (27) include
1,3,5-triisocyanatobenzene, 1,3,5-triisocyanato-2-methylbenzene,
1,3,5-tris(1-isocyanatopropane-2-yl)benzene,
1,3,5-tris(1-isocyanatopropane-2-yl)-2-methylbenzene,
1,3,5-tris(1-isocyanatomethyl)-2-methylbenzene, and
2,2'-((2-isocyanato-1,3-phenylene)bis(methylene))bis(isocyanatebenzene).

<Compound Having an Unsaturated Bond>

In addition to the difunctional or more-functional isocyanate compound, the isocyanate composition according to the present embodiment contains a compound having at least one unsaturated bond excluding unsaturated bonds constituting an aromatic ring, the compound being other than the isocyanate compound.

The compound having an unsaturated bond (hereinafter, may be referred to as "unsaturated bond compound") according to the present embodiment has at least one unsaturated bond excluding unsaturated bonds constituting an aromatic ring. The unsaturated bond is preferably an unsaturated bond between carbon atoms, an unsaturated bond between a carbon atom and a nitrogen atom, or an unsaturated bond between a carbon atom and an oxygen atom. From the viewpoint of the stability of the compound, the unsaturated bond is preferably a double bond, and more preferably a double bond between carbon atoms (C=C) or a double bond between a carbon atom and an oxygen atom (C=O). In addition, carbon atoms constituting the compound preferably bond with at least three atoms, respectively.

Although there is a general case where a double bond between carbon atoms is a double bond between carbon atoms constituting an aromatic ring, the unsaturated bond contained in the unsaturated bond compound in the isocyanate composition according to the present embodiment does not contain a double bond between carbon atoms constituting an aromatic ring.

Examples of the unsaturated bond compound include: compounds of the following formula (28); carbonic acid derivatives (such as N-unsubstituted carbamic acid ester, carbonate ester, and N-substituted carbamic ester), compounds having an UV absorption in an area of decamer or higher isocyanates in a measurement spectrum of gel permeation chromatography, compounds having an isocyanurate group and/or a biuret group, and compounds of the following formula (1). Among these, the unsaturated bond compound is preferably a compound having an UV absorption in an area of decamer or higher isocyanates in a measurement spectrum of gel permeation chromatography, or, a compound of the following formula (1).

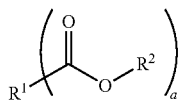

(1)

In the formula (1), $R^1$ represents a C2-10 aliphatic group or a C6-10 aromatic group, which may contain an isocyanate group, $R^2$ represents a C2-10 aliphatic group or a C6-25 aromatic group, which does not contain an isocyanate group, and a represents an integer of 1 or 2.

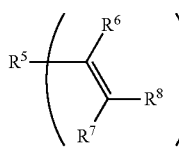

(28)

In the formula (28), $R^5$, $R^6$, $R^7$ and $R^8$ each independently represent a hydrogen atom, a halogen atom or a C1-10 organic group, $R^5$ to $R^8$ do not represent simultaneously hydrogen atoms, r represents 1 when $R^5$ represents a hydrogen atom or a halogen atom, and r represents an integer of 1 to 3 when $R^5$ represents a C1-10 organic group.

<Compound Having an UV Absorption in an Area of Decamer or Higher Isocyanates in a Measurement Spectrum of Gel Permeation Chromatography>

A compound having an UV absorption in an area of decamer or higher isocyanates in a measurement spectrum of gel permeation chromatography (GPC) is preferably a compound having a 1-nylon body structure of the following formula (37) as the main skeleton thereof.

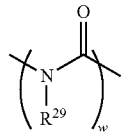

(37)

In the formula, $R^{29}$ represents a residual group obtained by removing one isocyanate group from the difunctional or more-functional isocyanate compound, and w represents an integer of 1 or more. The terminal groups thereof are not described.

The isocyanate constituting the compound having an UV absorption in an area of decamer or higher isocyanates in a measurement spectrum of gel permeation chromatography (GPC) may be the same as or different from an isocyante constituting the isocyanate composition according to the present embodiment, and may be selected from the isocyante compounds mentioned in the description regarding to the <difunctional or more-functional isocyanate compound>.

The compound is defined by the GPC measurement. Specifically, the compound exhibits a peak of UV absorption at the wavelength of 254 nm in the area of decamer or higher isocyanates when GPC is conducted using tetrahydrofuran as a developing solvent and polystyrene as a molecular weight analytical standard substance.

The concentration of the compound having an UV absorption in an area of decamer or higher isocyanates in a measurement spectrum of gel permeation chromatography (GPC) may be determined using a GPC equipped with a UV detector and a differential refractometer (the UV detector and the differential refractometer may be connected in parallel or in series) by conducting calculation of (B)/(A) wherein (A) represents the peak area corresponding to difunctional or more-functional isocyanate compounds in the differential refractive index, and (B) represents the peak area corresponding to a compound having a UV absorption (at the wavelength of 254 nm) in the area of decamer or higher isocyanates.

<Compound Having an Isocyanurate Group and/or a Biuret Group>

A compound having an isocyanurate group and/or a biuret group is a compound having a group of the following formula (6') or the formula (7').

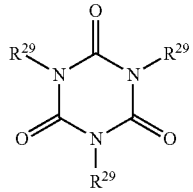

(6')

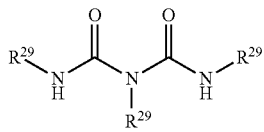
(7')

In the formulae, $R^{29}$ represents a residual group obtained by removing one isocyanate group from a difunctional or more-functional isocyanate compound.

An isocyanate constituting a compound having an isocyanurate group and/or a biuret group may be the same kind of an isocyanate as that of an isocyanate compound constituting the isocyanate composition according to the present embodiment or a different kind of an isocyanate therefrom, and may be selected from isocyanate compounds mentioned in the description regarding to the <difunctional or more-functional isocyanate compound>. The amount of the compound having an isocyanurate group and/or a biuret group in the isocyanate composition may be an addition amount of the compound having an isocyanurate group and/or a biuret group or an amount determined by GPC conducted using tetrahydrofuran as a developing solvent. In the method for determining the amount by GPC, the amount may be specifically determined by GPC equipped with a differential refractometer by conducting calculation of (B)/(A) wherein (A) represents the peak area corresponding to an isocyanate compounds in the differential refractive index, and (B) represents the peak area corresponding to a compound having an isocyanurate group and/or a biuret group.

<Compound of Formula (1)>

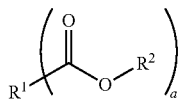
(1)

In the formula, $R^1$ represents a C2-10 aliphatic group or a C6-10 aromatic group, which may have an isocyanate group, $R^2$ represents a C2-10 aliphatic group or a C6-25 aromatic group, which does not contain an isocyanate group, and a represents an integer of 1 or 2.

In the formula (1), $R^1$ represents a C2-10 aliphatic group or a C6-10 aromatic group, examples of the aliphatic group include: residual groups obtained by removing the number a of hydrogen atoms from compounds such as methane, ethane, propane, butane, heptane, hexane, octane, nonane, or decane, examples of the aromatic group include residual groups obtained by removing the number a of hydrogen atoms from compounds, such as benzene, methylbenzene, ethylbenzene, butylbenzene, octylbenzene, nonylbenzene, diphenyl, terphenyl, phenylpropyl benzene, di(phenylpropyl)benzene, or diphenylether. Among these, $R^1$ is preferably a residual group obtained by removing the number a of hydrogen atoms from a C2-10 alkane or benzene.

In the formula (1), $R^2$ represents a C2-15 aliphatic group or a C6-25 aromatic group, which does not contain an isocyanate group, and preferably represents a C5-15 alkyl group.

Specific examples of the compound include ethyl acetate, butyl acetate, hexyl acetate, methyl propionate, ethyl butyrate, butyl butyrate, ethyl valerate, butyl valerate, ethyl hexanoate, ethyl octanoate, butyl caprate, phenyl acetate, benzyl acetate, methyl benzoate, ethyl benzoate, phenyl benzoate, benzyl benzoate, diethyl phthalate, dibutyl phthalate, benzyl butyl phthalate, di-2-ethylhexyl phthalate, diisodecyl adipate, and triisodecyl trimellitate.

In the formula (1), $R^1$ may contain an isocyanate group, and, specifically, the compound of the formula (1) may be a compound of the following formula (38) or (39).

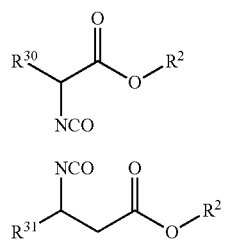

In the formulae, $R^2$ represents a group defined in the formula (1), $R^{30}$ represents a hydrogen atom, a C1-8 aliphatic group, or a C6-8 aromatic group, which may further contain an isocyanate group, and $R^{3'}$ represents a hydrogen atom, a C1-7 aliphatic group, or a C6-7 aromatic group, which may further contain an isocyanate group.

In the case where the compound of the formula (1) has the same structure as that of the isocyanate compound in the composition according to the present embodiment, the compound is defined as the isocyanate compound.

Specific examples thereof include compounds of the following formulae.

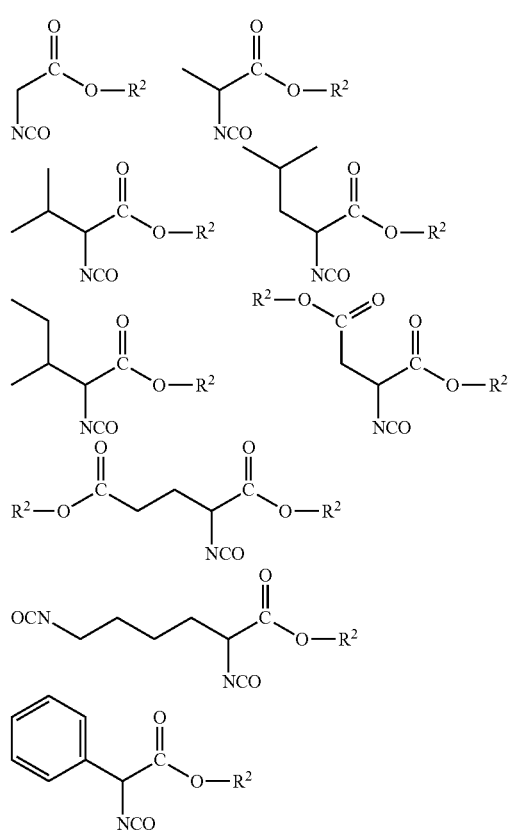

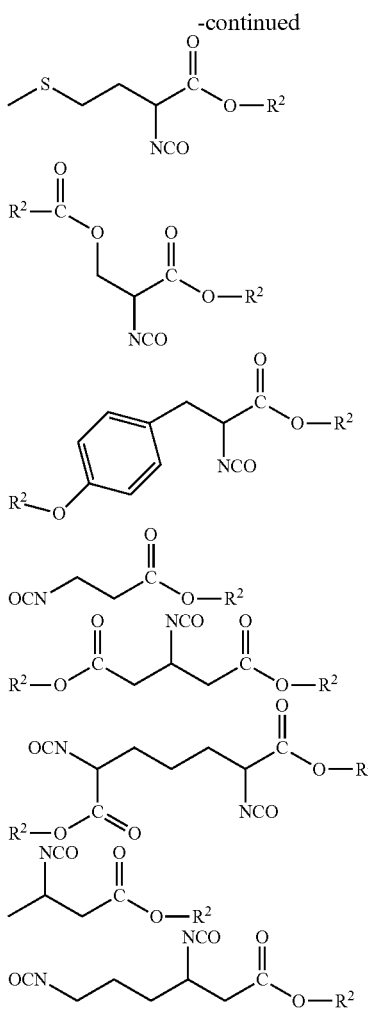

In the case where the compound of the formula (1) has the same structure as that of the isocyanate compound in the composition according to the present embodiment, the compound is defined as an isocyanate compound.

<Compound of Formula (28)>

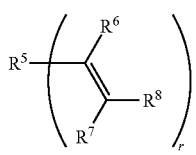

In the formula (28), $R^5$, $R^6$, $R^7$ and $R^8$, each independently represent a hydrogen atom, a halogen atom, or a C1-10 organic group, $R^5$ to $R^8$ do not represent simultaneously hydrogen atoms, r represents 1 when $R^5$ represents a hydrogen atom or a halogen atom, and r represents an integer of 1 to 3 when $R^5$ represents a C1-10 organic group.

In the compound of the formula (28), $R^5$ preferably represents a hydrogen atom or a C1-10 organic group. When $R^5$ represents an organic group, $R^5$ preferably represents a C1-10 aliphatic group or a C6-10 aromatic group.

Examples of such $R^5$ include: groups obtained by removing the number r of hydrogen atoms from alkanes such as methane, ethane, propane, butane, pentane, hexane, heptane, octane, nonane, decane, or structural isomers thereof; groups obtained by removing the number r of hydrogen atoms from cycloalkanes, such as cyclopentane, cyclohexane, cyclopentane, and cyclooctane; groups obtained by removing the number r of hydrogen atoms from cabin alkyl group-substituted cycloalkanes, such as methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof; and groups obtained by removing the number r of hydrogen atoms from aromatic compounds, such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof. Among these, $R^5$ preferably represents a group obtained by removing the number r of hydrogen atoms from a C1-10 alkane or a benzene.

$R^6$ to $R^8$ preferably represent hydrogen atoms or C1-10 organic groups.

When $R^6$ to $R^8$ represent organic groups, $R^6$ to $R^8$ preferably represent C1-10 aliphatic groups or C6-10 aromatic groups. Examples of such $R^6$ to $R^8$ include: alkyl groups, such as a methyl group, an ethyl group, a propyl group, a butyl group, a pentyl group, a hexyl group, a heptyl group, an octyl group, a nonyl group, a decyl group, and structural isomers thereof; cahin alkyloxy groups, such as a methyloxy group, an ethyloxy group, a propyloxy group, a butyloxy group, a pentyloxy group, a hexyloxy group, a heptyloxy group, an octyloxy group, a nonyloxy group, a decyl oxy group, and structural isomers thereof; cycloalkyl groups, such as a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; groups constituted by chain alkyl groups and cycloalkyl groups; groups formed by removing one hydrogen atom from aromatic compounds such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof. Among these, it is preferable that $R^6$ to $R^8$ represent C1-10 alkyl groups.

Specific examples of the compound of formula (28) include: propene, butene, pentene, 2-methylbutene, 2,4,4-trimethylpentene, hexene, octene, nonene, decene, hexadecene, octadecene, butadiene, pentadiene, hexadiene, chloroethylene, chloropropene, chlorobutene, chloropentene, chlorohexene, chlorooctene, chlorononene, chlorodecene, chlorohexadecene, chlorooctadecene, chlorobutadiene, chloropentadiene, chlorohexadiene, dichloroethylene, dichloropropene, dichlorobutene, dichloropentene, dichlorohexene, dichlorooctene, dichlorononene, dichlorodecene, dichlorohexadecene, dichlorooctadecene, dichlorobutadiene, dichloropentadiene, dichlorohexadiene, bromoethylene, bromopropene, bromobutene, bromopentene, bromohexene, bromooctene, bromononene, bromodecene, bromohexadecene, bromooctadecene, bromobutadiene, bromopentadiene, bromohexadiene, dibromoethylene, dibromopropene, dibromobutene, dibromopentene, dibromohexene, dibromooctene, dibromononene, dibromodecene, dibromohexadecene, dibromooctadecene, dibromobutadiene, dibromopentadiene, dibromohexadiene, fluoroethylene, fluoropropene, fluorobutene, fluoropentene, fluorohexene, fluorooctene, fluorononene, fluorodecene, fluorohexadecene, fluorooctadecene, fluorobutadiene, fluoropentadiene, fluorohexadiene, difluoroethylene, difluoropropene, difluorobutene, difluoropentene, difluorohexene, difluorooctene, difluorononene, difluorodecene, difluorohexadecene, difluorooctadecene, difluorobutadiene, difluoropentadiene, difluorohexadiene, styrene, propenylbenzene, isopropenylbenzene (also referred to as "α-methylstyrene"), allylbenzene, phenylbutadiene, divinylbenzene, stilbene, vinylanisole, propenylanisole, allylanisole, isoanethole, elemicin, asarone, chlorostyrene, chloropropenylbenzene, chloroisopropenylbenzene, chloroallylbenzene, chlorophenylbutadiene, chlorodivinylbenzene, chlorostilbene, chlorovinylanisole, chloropropenylanisole, chloroallylanisole, chloroisoanethole, chloroelemicin, chloroasarone, bromostyrene, bromopropenylbenzene, bromoisopropenylbenzene, bromoallylbenzene, bromophenylbutadiene, bromodivinylbenzene, bromostilbene, bromovinylanisole, bromopropenylanisole, bromoallylanisole, bromoisoanethole, bromoelemicin, bromoasarone, fluorostyrene, fluoropropenylbenzene, fluoroisopropenylbenzene, fluoroallylbenzene, fluorophenylbutadiene, fluorodivinylbenzene, fluorostilbene, fluorovinylanisole, fluoropropenylanisole, fluoroallylanisole, fluoroisoanethole, fluoroelemicin, fluoroasarone, dichlorostyrene, dichloropropenylbenzene, dichloroisopropenylbenzene, dichloroallylbenzene, dichlorophenylbutadiene, dichlorodivinylbenzene, dichlorostilbene, dichlorovinylanisole, dichloropropenylanisole, dichloroallylanisole, dichloroisoanethole, dichloroelemicin, dichloroasarone, dibromostyrene, dibromopropenylbenzene, dibromoisopropenylbenzene, dibromoallylbenzene, dibromophenylbutadiene, dibromodivinylbenzene, dibromostilbene, dibromovinylanisole, dibromopropenylanisole, dibromoallylanisole, dibromoisoanethole, dibromoelemicin, dibromoasarone, difluorostyrene, difluoropropenylbenzene, difluoroisopropenylbenzene, difluoroallylbenzene, difluorophenylbutadiene, difluorodivinylbenzene, difluorostilbene, difluorovinylanisole, difluoropropenylanisole, difluoroallylanisole, difluoroisoanethole, difluoroelemicin, difluoroasarone, and structural isomers thereof.

<Carbonic Acid Derivative>

A carbonic acid derivative used in the isocyanate composition according to the present embodiment is represented by the following formula (29).

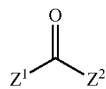

(29)

In the formula (29), $Z^1$ and $Z^2$ each independently represent a residual group obtained by removing a hydrogen atom from a hydroxy compound or an amino group which may be substituted with an organic group.

Examples of the compound of the formula (29) include urea compounds, N-unsubstituted carbamic acid esters, carbonate esters, and, N-substituted carbamic acid esters.

<<Urea Compound>>

The urea compound is a compound having at least one urea bond in a molecule thereof. The urea compound used in the isocyanate composition according to the present embodiment is preferably a compound having one urea bond, and is represented by the following formula (30).

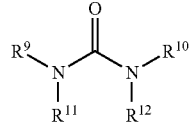

(30)

In the formula (30), $R^9$, $R^{10}$, $R^{11}$ and $R^{12}$ each independently represent a C1-20 aliphatic group, a C7-20 aliphatic group substituted with an aromatic compound, a C6-20 aromatic group or a hydrogen atom, the sum of the number of carbons constituting $R^9$ and $R^{11}$ is an integer of 0 to 20, and the sum of the number of carbons constituting $R^0$ and $R^2$ is an integer of 0 to 20.

Specific examples of $R^9$, $R^{10}$, $R^{11}$ and $R^{12}$ in the formula (30) include: a hydrogen atom; chain alkyl groups such as a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, and a nonadecyl group; C6-20 aromatic groups such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a duheptylphenyl group, a terphenyl group, a trimethylphenyl group, a triethylphenyl group, a tripropylphenyl group, and a tributylphenyl group; and C7-20 aralkyl groups such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Examples of the urea compound of the formula (30) include urea, methylurea, ethylurea, propylurea, butylurea, pentylurea, hexylurea, heptylurea, octylurea, nonylurea, decylurea, undecylurea, dodecylurea, tridecylurea, tetradecylurea, pentadecylurea, hexadecylurea, heptadecylurea, octadecylurea, nonadecylurea, phenylurea, N-(methylphenyl)urea, N-(ethylphenyl)urea, N-(propylphenyl)urea, N-(butylphenyl)urea, N-(pentylphenyl)urea, N-(hexylphenyl)urea, N-(heptylphenyl)urea, N-(octylphenyl)urea, N-(nonylphenyl)urea, N-(decylphenyl)urea, N-biphenylurea, N-(dimethylphenyl)urea, N-(diethylphenyl)urea, N-(dipropylphenyl)urea, N-(dibutylphenyl)urea, N-(dipentylphenyl)urea, N-(dihexylphenyl)urea, N-(diheptylphenyl) urea, N-terphenylurea, N-(trimethylphenyl)urea, N-(triethylphenyl)urea, N-(tripropylphenyl)urea, N-(tributylphenyl) urea, N-(phenylmethyl)urea, N-(phenylethyl)urea, N-(phenylpropyl)urea, N-(phenylbutyl)urea, N-(phenylpentyl)urea, N-(phenylhexyl)urea, N-(phenylheptyl)urea, N-(phenyloctyl)urea, N-(phenylnonyl)urea, dimethylurea, diethylurea, dipropylurea, dibutylurea, dipentylurea, dihexylurea, diheptylurea, dioctylurea, dinonylurea, didecylurea, diundecylurea, didodecylurea, ditridecylurea, ditetradecylurea, dipentadecylurea, dihexadecylurea, diheptadecylurea, dioctadecylurea, dinonadecyl, diphenylurea, di(methylphenyl)urea, di(ethylphenyl)urea, di(propylphenyl)urea, di(butylphenyl)urea, di(pentylphenyl)urea, di(hexylphenyl)urea, di(heptylphenyl)urea, di(octylphenyl)urea, di(nonylphenyl)urea, di(decylphenyl)urea, di(biphenyl) urea, di(dimethylphenyl)urea, di(diethylphenyl)urea, di(dipropylphenyl)urea, di(dibutylphenyl)urea, di(dipentylphenyl)urea, di(dihexylphenyl)urea, di(diheptylphenyl) urea, di(terphenyl)urea, di(trimethylphenyl)urea, di(triethylphenyl)urea, di(tripropylphenyl)urea, di(tributylphenyl) urea, di(phenylmethyl)urea, di(phenylethyl)urea, di(phenylpropyl)urea, di(phenylbutyl)urea, di(phenylpentyl) urea, di(phenylhexyl)urea, di(phenylheptyl)urea, di(phenyloctyl)urea, and di(phenylnonyl)urea.

Among these, $R^9$, $R^{10}$, $R^{11}$ and $R^{12}$ in the formula (30) preferably represent hydrogen atoms.

<<N-Unsubstituted Carbamic Acid Ester>>

A compound of the following formula (31) is preferably used as a N-unsubstituted carbamic acid ester.

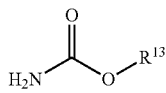

(31)

In the formula (31), $R^{13}$ represents a C1-20 aliphatic group, a C7-20 aliphatic group substituted with an aromatic group, or a C6-20 aromatic group.

Examples of the aliphatic group of $R^{13}$ in the formula (31) include groups that are free from an active hydrogen and are constituted by chain hydrocarbon groups, cyclichydrocarbon groups, or both chain hydrocarbon groups and cyclichydrocarbon groups.

The aliphatic group of $R^{13}$ may contain atoms other than carbon and hydrogen, and the atoms are preferably specific nonmetallic atoms (such as oxygen, nitrogen, sulfur, silicon or halogen atoms).

The aliphatic group of $R^{13}$ is preferably an aliphatic group containing an oxygen atom as the atom other than carbon and hydrogen or an aliphatic group free from any atoms other than carbon and hydrogen.

Examples of the aliphatic group substituted with an aromatic group of $R^{13}$ include groups in which C1-14 chain or branched-chain alkyl groups are substituted with C6-19 aromatic groups.

The aliphatic group substituted with an aromatic group may contain atoms other than carbon and hydrogen.

The chain or branched chain alkyl group is a group free from an active hydrogen, and may contain an atom other than carbon and hydrogen, and the atom is preferably a specific nonmetallic atom (an oxygen, nitrogen, sulfur, silicon, or halogen atom).

Examples of the aromatic group include groups free from an active hydrogen, and preferable examples thereof include monocyclic aromatic groups, condensed polycyclic aromatic groups, cross-linked cyclic aromatic groups, ring-assembly aromatic groups, and heterocyclic aromatic groups. The aromatic group may contain an atom other than carbon and hydrogen, and the atom other than hydrogen is preferably a specific nonmetallic atom (an oxygen, nitrogen, sulfur, silicon, or a halogen atom). The aromatic group is preferably a substituted or unsubstituted phenyl group, a substituted or unsubstituted naphthyl group, or a substituted or unsubstituted anthryl group. The aliphatic group and the aromatic group are preferably groups that contain an oxygen atom as an atom other than carbon and oxygen, or hydrocarbon groups free from any atoms other than carbon and hydrogen.

Examples of the substituent group include a hydrogen atom, aliphatic groups (such as chain hydrocarbon groups, cyclichydrocarbon groups, and groups constituted by chain hydrocarbon groups and cyclichydrocarbon groups), and groups constituted by aliphatic groups and aromatic groups.

Specific examples of $R^{13}$ include: C1-50 chain alkyl groups such as a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and an eicosyl group; C6-50 aromatic groups such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, and a tributylphenyl group; and C7-50 aralkyl groups such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specific examples of the N-unsubstituted carbamic acid ester of the formula (31) include a methyl carbmate, ethyl carbmate, propyl carbmate, butyl carbmate, pentyl carbmate, hexyl carbmate, heptyl carbmate, octyl carbmate, nonyl carbmate, decyl carbmate, undecyl carbmate, dodecyl carbmate, tridecyl carbmate, tetradecyl carbmate, pentadecyl carbmate, hexadecyl carbmate, heptadecyl carbmate, octadecyl carbmate, nonadecyl carbmate, phenyl carbmate, (methylphenyl)carbmate, (ethylphenyl) carbmate, (propylphenyl)carbmate, (butylphenyl)carbmate, (pentylphenyl) carbmate, (hexylphenyl)carbmate, (heptylphenyl)carbmate, (octylphenyl)carbmate, (nonylphenyl)carbmate, (decylphenyl)carbmate, (biphenyl) carbmate, (dimethylphenyl)carbmate, (diethylphenyl)carbmate, (dipropylphenyl)carbmate, (dibutylphenyl)carbmate, (dipentylphenyl)carbmate, (dihexylphenyl)carbmate, (diheptylphenyl)carbmate, (terphenyl) carbmate, (trimethylphenyl)carbmate, (triethylphenyl)carbmate, (tripropylphenyl)carbmate, (tributylphenyl)carbmate, (phenylmethyl)carbmate, (phenylethyl)carbmate, (phenylpropyl)carbmate, (phenylbutyl)carbmate, (phenylpentyl) carbmate, (phenylhexyl)carbmate, (phenylheptyl)carbmate, (phenyloctyl)carbmate, (phenylnonyl)carbmate and structural isomers thereof.

<<Carbonate Ester>>

In the present specification, the term "carbonate ester" means a compound obtained by substituting one or two hydrogen atom of carbonic acid ($CO(OH)_2$) with an aliphatic group or an aromatic group.

In the isocyanate composition according to the present embodiment, a compound of the following formula (32) is preferably used.

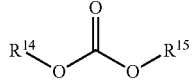

(32)

In the formula (32), $R^{14}$ and $R^{15}$ each independently represent a C1-20 aliphatic group, a C7-20 aliphatic group substituted with an aromatic group, or a C6-20 aromatic group.

Examples of $R^{14}$ and $R^{15}$ include the same groups as those of $R^{13}$ of the formula (31). Among these, it is preferable that $R^{14}$ and $R^{15}$ each independently represent a C1-6 alkyl group or a phenyl group.

Specific examples of the carbonate ester of the formula (32) include dimethyl carbonate, diethyl carbonate, dipropyl carbonate, dibutyl carbonate, dipentyl carbonate, dihexyl carbonate, diheptyl carbonate, dioctyl carbonate, dinonyl carbonate, didecyl carbonate, diundecyl carbonate, didodecyl carbonate, ditridecyl carbonate, ditetradecyl carbonate, dipentadecyl carbonate, dihexadecyl carbonate, diheptadecyl carbonate, dioctadecyl carbonate, dinonadecyl carbonate, diphenyl carbonate, di(methylphenyl)carbonate, di(ethylphenyl)carbonate, di(propylphenyl)carbonate, di(butylphenyl)carbonate, di(pentylphenyl)carbonate, di(hexylphenyl)carbonate, di(heptylphenyl)carbonate, di(octylphenyl)carbonate, di(nonylphenyl)carbonate, di(decylphenyl)carbonate, di(biphenyl)carbonate, di(dimethylphenyl)carbonate, di(diethylphenyl)carbonate, di(dipropylphenyl)carbonate, di(dibutylphenyl)carbonate, di(dipentylphenyl)carbonate, di(dihexylphenyl)carbonate, di(diheptylphenyl)carbonate, di(phenylphenyl)carbonate, di(trimethylphenyl)carbonate, di(triethylphenyl)carbonate, di(tripropylphenyl)carbonate, di(tributylphenyl)carbonate, di(phenylmethyl)carbonate, di(phenylethyl)carbonate, di(phenylpropyl)carbonate, di(phenylbutyl)carbonate, di(phenylpentyl)carbonate, di(phenylhexyl)carbonate, di(phenylheptyl)carbonate, di(phenyloctyl)carbonate, di(phenylnonyl)carbonate and structural isomers thereof. Among these, di(C1-6 alkyl)carbonates, (C1-6 alkylphenyl) carbonate, and diphenyl carbonate are preferable.

<<N-Substituted Carbamic Acid Ester>>

Examples of a N-substituted carbamic acid ester include compounds of formula (33). The N-substituted carbamic acid ester is also one of more preferable aspects of the compound of the formula (1).

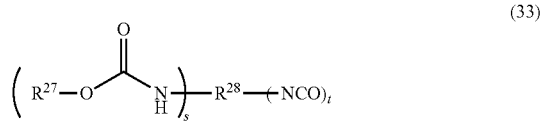

(33)

In the formula (33), $R^{28}$ represents a residual group obtained by removing an isocyanate group from the isocyanate compound, R represents an organic group, s represents an integer of 1 to c, wherein c represents the number of isocyanate groups of the isocyanate compound, and t represents an integer obtained by subtracting s from c. $R^{28}$ preferably represents a residual group obtained by removing an isocyanate group from the isocyanate compound of the formula (24), (25), (26), or (27).

As is apparent from the description of the formula (33), c depends on the number of isocyanate groups of the isocyanate compound constituting the isocyanate composition according to the present embodiment. When the isocyanate compound is a trifunctional isocyanate compound, c represents 3, and when the isocyanate compound is a pentafunctional isocyanate compound, c represents 5. When $R^{28}$ is an isocyanate compound of the formula (24), (25), (26) or (27), c represents 3. As is apparent from the fact that the isocyanate compound is a difunctional or more-functional isocyanate compound in the isocyanate composition according to the present embodiment, c represents an integer of 2 or more.

$R^{27}$ is derived from a hydroxy compound, and may be a residual group obtained by removing a hydroxyl group (—OH) constituting a hydroxy compound. Hereinafter, $R^{27}$ is defined as a hydroxyl compound in which a hydroxyl group is added to $R^{27}$ ($R^{27}OH$) so as to explain $R^{27}$ simply.

The hydroxy compound ($R^{27}OH$) may be an alcohol or an aromatic hydroxy compound. When the hydroxy compound ($R^{27}OH$) is an alcohol, the hydroxy compound is a compound of formula (34).

$R^{16}(OH)u$ (34)

In the formula (34), $R^{16}$ represents a group substituted with the number u of hydroxy groups, the group being constituted by a C1-20 aliphatic group or a C7-20 aliphatic group bonded with an aromatic group, and u represents an integer of 1 to 3. $R^{16}$ is a group free from an active hydrogen other than the hydroxy groups.

Examples of the aliphatic group as $R^{16}$ in the formula (34) include chain hydrocarbon groups, cyclichydrocarbon groups, and groups in which chain hydrocarbon groups and cyclichydrocarbon groups are bonded (such as cyclichydrocarbon groups substituted with chain hydrocarbon groups, or chain hydrocarbon groups substituted with cyclichydrocarbon groups).

The aliphatic group as $R^{16}$ may contain an atom other than carbon atoms and hydrogen atoms, and the atom is preferably a specific nonmetallic atom (such as an oxygen, nitrogen, sulfur, silicon, or halogen atom). The aliphatic group as $R^{16}$ is preferably an aliphatic group containing an oxygen as an atom other than carbon and hydrogen or an aliphatic group free from atoms other than carbon and hydrogen.

Examples of the aliphatic group bonded with an aromatic group include: alkyl groups and cycloalkyl groups, which are bonded with a C6-12 aromatic group. Examples of the aromatic group bonded with the aliphatic group include monocyclic aromatic groups, condensed polycyclic aromatic groups, crosslinked cyclic aromatic groups, ring-assembly aromatic groups, and heterocyclic aromatic groups. The aromatic group is preferably a substituted or unsubstituted phenyl group, a substituted or unsubstituted naphthyl group, or a substituted or unsubstituted anthryl group. The aromatic group may contain atoms other than carbon atoms and hydrogen atoms, and the atoms other than hydrogen atom are preferably specific nonmetallic atoms (such as oxygen, nitrogen, sulfur, silicon, or halogen atoms).

Specific examples of such $R^{16}$ include: chain alkyl groups such as a methyl group, an ethyl group, a propyl group, a butyl group, a pentyl group, a hexyl group, a heptyl group, an octyl group, a nonyl group, a decyl group, a dodecyl group, an octadecyl group and structural isomers thereof; cycloalkyl groups such as a cyclopentyl group, a cyclohexyl group, a cycloheptyl group, a cyclooctyl group, an structural isomers thereof; groups constituted by chain alkyl groups and cycloalkyl groups, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group and structural isomers thereof; and aralkyl groups such as a phenylmethyl group, a phenylethyl group, a phenylpropyl group, a phenylbutyl group, a phenylpentyl group, a phenylhexyl group, a phenylheptyl group, a phenyloctyl group, a phenylnonyl group and structural isomers thereof. Among these, $R^{16}$ is preferably a C1-10 alkyl group or a C3-10 cycloalkyl group.

In view of the industrial use, when the alcohol is used to produce the compound of the formula (34), an alcohol having one or two alcoholic hydroxy group (hydroxyl group directly added to a carbon atom constituting the hydroxy compound, the carbon atom not constituting an aromatic ring) is preferable because of the low viscosity generally, and a monoalcohol having one alcoholic hydroxy group is more preferable.

Specific examples of the alcohol include: unsubstituted alkyl alcohols such as methyl alcohol, ethyl alcohol, propyl alcohol, butyl alcohol, pentyl alcohol, hexyl alcohol, heptyl alcohol, octyl alcohol, nonyl alcohol, decyl alcohol, dodecyl alcohol, octadecyl alcohol, and structural isomers thereof; unsubstituted cycloalkyl alcohols such as cyclopentyl alcohol, cyclohexyl alcohol, cycloheptyl alcohol, cyclooctyl alcohol, and structural isomers thereof; alcohols constituted by chain alkyl groups and cycloalkyl alcohols, such as methylcyclopentyl alcohol, ethylcyclopentyl alcohol, methylcyclohexyl alcohol, ethylcyclohexyl alcohol, propylcyclohexyl alcohol, butylcyclohexyl alcohol, pentylcyclohexyl alcohol, hexylcyclohexyl alcohol, dimethylcyclohexyl alcohol, diethylcyclohexyl alcohol, dibutylcyclohexyl alcohol, and structural isomers thereof; and alkyl alcohols substituted with aromatic groups, such as phenylmethyl alcohol, phenylethyl alcohol, phenylpropyl alcohol, phenylbutyl alcohol, phenylpentyl alcohol, phenylhexyl alcohol, phenylheptyl alcohol, phenyloctyl alcohol, phenylnonyl alcohol, and structural isomers thereof.

In the case where the hydroxy compound ($R^{27}OH$) is an aromatic hydroxy compound, monofunctional to trifunctional (that is, the number of hydroxyl groups bonded with an aromatic ring is an integer of 1 to 3) aromatic hydroxy compound is preferable, because of the industrial availability and low viscosity, generally. Examples of the aromatic hydroxy compound include compounds of the following formula (35).

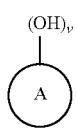

(35)

In the formula (35), the ring A represents an aromatic hydrocarbon ring which may have a substituent group, the ring A may be a monocyclic or polycyclic, and v represents an integer of 1 to 3.

Among the aromatic hydroxy compounds of the formula (35), monovalent aromatic hydroxy compounds wherein v is 1 is more preferable.

As the substituent group which the ring A may have, halogen atoms, aliphatic groups and aromatic groups can be mentioned. Examples of the substituent group include cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, and side chain-containing cyclic hydrocarbon group), heterocyclic groups, heterocyclic spiro groups, and hetero cross-linked cyclic groups, acyclic hydrocarbon groups, and groups formed by binding at least one acyclic hydrocarbon group and at least one cyclic group.

Among these substituent groups, the substituent groups preferably used according to the present embodiment in view of the difficulty in occurrence of side reactions are groups selected from the group consisting of acyclic hydrocarbon groups, cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, and side chain-containing cyclic hydrocarbon group) or groups bonded with at least two groups selected from the above-mentioned group (groups mutually substituted).

Preferable substituent groups that substitute the ring A are groups selected from the group consisting of alkyl groups, cycloalkyl groups, aryl groups, aralkyl groups, and ether groups (substituted or unsubstituted, alkyl ethers, aryl ethers or aralkyl ethers); groups formed by binding at least two groups selected from the above-mentioned group with each other, groups formed by binding at least two groups selected from the above-mentioned group via a saturated hydrocarbon bond or an ether bond; or halogen atoms, provided that the sum of the number of carbon atoms constituting the ring A and the number of carbon atoms constituting all substituent groups that substitute the ring A is an integer of 6 to 50.

Examples of the ring A include a benzene ring, a naphthalene ring, a anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring. The ring A preferably include at least one structure selected from a benzene ring and a naphthalene ring.

When the aromatic hydroxyl compound is used to prepare the compound of the formula (33), an aromatic hydroxy compound having an easily-available benzene ring as a skeleton is preferable from the viewpoint of industrial use. Examples of the aromatic hydroxy compound include an aromatic hydroxy compound of the following formula (36).

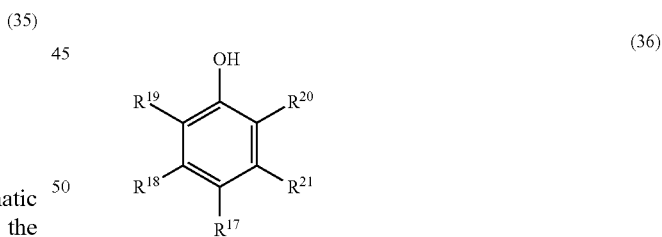

(36)

In the formula (36), $R^{17}$, $R^{18}$, $R^{19}$, $R^{20}$ and $R^{21}$ each independently represent a group selected from the group consisting of a chain alkyl group, a cycloalkyl group, an aryl group, a chain alkyl group bonded with an aromatic group, a cycloalkyl group bonded with an aromatic group, and an ether group (substituted or unsubstituted alkyl ether, aryl ether, or alkyl ether substituted with an aromatic group); a group formed by binding at least two groups selected from the above-mentioned group with each other; a group formed by binding at least two groups selected from the above-mentioned group via a saturated aliphatic bond or an ether bond; a halogen atom; or a hydrogen atom, and the sum of the number of carbon atoms constituting $R^{17}$ to $R^{21}$ is an integer of 0 to 44.

In the formula (36), preferred $R^{17}$ to $R^{21}$ are groups independently selected from groups shown in the following (i) to (v):
(i) hydrogen atom;
(ii) halogen atoms;
(iii) C1-44 carbon functional groups in which a carbon atom at the position α bonds with at least one group selected from the group consisting of C1-43 chain alkyl groups, C1-43 cycloalkyl groups, C1-43 alkoxy groups, C2-43 polyoxyalkylene alkyl ether groups free from hydroxy groups at the terminal ends thereof, C6-43 aryl groups, C7-43 allyl groups bonded with an aromatic group, C7-43 cycloalkyl groups bonded with an aromatic group and a C7-43 alkyloxy groups bonded with an aromatic group;
(iv) C1-44 aromatic groups, bonded with at least one group selected from the group consisting of a hydrogen atom, C1-38 chain alkyl groups, C4-38 cycloalkyl groups, C1-38 alkoxy groups, C2-38 polyoxyalkylene alkyl ether groups free from hydroxy groups at the terminal ends thereof, C6-38 aromatic groups, C7-38 alkyl groups bonded with an aromatic group, C7-38 cycloalkyl groups bonded with an aromatic group, and C7-38 alkyloxy groups bonded with an aromatic group;
(v) C1-44 oxygen functional groups, an oxygen atom of which is bonded with at least one group selected from the group consisting of C1-44 alkyl groups, C1-44 cycloalkyl groups, C1-44 alkoxy groups, C2-44 polyoxyalkylene alkyl ether groups free from hydroxy groups at the terminal ends thereof, C6-44 aromatic groups, C7-44 alkyl groups bonded with an aromatic group, and C7-44 aralkyloxy groups.

Here, the term "aralkyloxy group" means a group in which an oxygen atom is bonded to the aralkyl group defined above.

Specific examples of $R^{17}$ to $R^{21}$ include: chain alkyl groups, such as a methyl group, an ethyl group, a propyl group, a butyl group, a pentyl group, a hexyl group, a heptyl group, an octyl group, a nonyl group, a decyl group, a dodecyl group, an octadecyl group, and structural isomers thereof; cycloalkyl groups, such as a cyclopentyl group, a cyclohexyl group, a cycloheptyl group, and a cyclooctyl group; groups constituted by chain alkyl groups and cycloalkyl groups, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; chain alkyloxy groups, such as a methoxy group, an ethoxy group, a propoxy group, a butyloxy group, a pentyloxy group, a hexyloxy group, a heptyloxy group, an octyloxy group, a nonyloxy group, a decyloxy group, a dodecyloxy group, an octadecyloxy group, and structural isomers thereof; cycloalkyloxy groups, such as a cyclopentyloxy group, a cyclohexyloxy group, a cycloheptyloxy group, and a cyclooctyloxy group; alkyloxy groups corresponding to the groups constituted by chain alkyl groups and cycloalkyl groups, such as a methylcyclopentyloxy group, an ethylcyclopentyloxy group, a methylcyclohexyloxy group, an ethylcyclohexyloxy group, a propyl cyclohexyloxy group, a butylcyclohexyloxy group, a pentylcyclohexyloxy group, a hexylcyclohexyloxy group, a dimethylcyclohexyloxy group, a diethylcyclohexyloxy group, a dibutylcyclohexyloxy group, and structural isomers thereof; aromatic groups, such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, a tributylphenyl group, and structural isomers thereof; groups constituted by aromatic groups and alkyl groups, such as a 1-methyl-1-phenylethyl group, and a 1-phenylethyl group; aromatic-oxy groups, such as a phenoxy group, a methylphenoxy group, an ethylphenoxy group, a propylphenoxy group, a butylphenoxy group, a pentylphenoxy group, a hexylphenoxy group, a heptylphenoxy group, an octylphenoxy group, a nonylphenoxy group, a decylphenoxy group, a phenylphenoxy group, a dimethylphenoxy group, a diethylphenoxy group, a dipropylphenoxy group, a dibutylphenoxy group, a dipentylphenoxy group, a dihexylphenoxy group, a diheptylphenoxy group, a diphenylphenoxy group, a trimethylphenoxy group, a triethylphenoxy group, a tripropylphenoxy group, a tributylphenoxy group, and structural isomers thereof; aralkyl groups, such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group; and aralkyloxy groups, such as a phenylmethoxy group, a phenylethoxy group, a phenylpropyloxy group, a phenylbutyloxy group, a phenylpentyloxy group, a phenylhexyloxy group, a phenylheptyloxy group, a phenyloctyloxy group, a phenylnonyloxy group, and structural isomers thereof. Among these, it is preferable that $R^{17}$ to $R^{21}$ each independently represent a hydrogen atom, a C1-10 alkyl group, a phenoxy group, or a C7-10 aralkyl group.

The compound of the formula (33) may be produced by reacting the difunctional or more-functional isocyanate compound and the hydroxy compound, as described above. Various compounds are produced depending the combination of s and t in the formula (33), because the difunctional or more-functional isocyanate compound is used. However, in the isocyanate composition according to the present embodiment, these compounds do not need to be distinguished to adjust the addition amount. For example, a trifunctional isocyanate is mixed with a hydroxyl compound at a stoichiometric ratio, relative to the trifunctional isocyanate, of 1 to 3, to produce a compound of the formula (33), and the resultant compound may be used without conducting purification to produce the isocyanate composition according to the present embodiment.

<Inert Compound>

The isocyanate composition according to the present embodiment may further contain an inert compound, which is at least one compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound not having a double bond between carbon atoms or between a carbon atom and an oxygen atom excluding unsaturated bonds constituting an aromatic ring (hereinafter, may be referred to as "inert compound), in an amount of 1.0 ppm by mass to $1.0 \times 10^4$ ppm by mass, based on the isocyanate compound. The inert compound does not react with the isocyanate compound during storing the isocyanate composition or reaction to produce the polyurethane.

The inert compounds are classified into compounds A to G. The hydrocarbon compounds are classified into the compound A and the compound B, the ether compounds and sulfide compounds are classified into the compounds C to E, the halogenated hydrocarbon compounds are classified into the compound F, the silicon-containing hydrocarbon compounds, the silicon-containing ether compounds and the silicon-containing sulfide compounds are classified into the compound G. The compounds A to G do not contain any unsaturated bonds other than an aromatic ring, and do not fall into the category of "compound having at least one unsaturated bond".

(Compound A)

The compound A is an aliphatic hydrocarbon compound having a liner chain, branched chain, or cyclic structure. The compound A is preferably a C5-20 hydrocarbon compound. Specific examples of the compound A include: pentane, hexane, heptane, octane, nonane, decane, dodecane, tetradecane, pentadecane, hexadecane, octadecane, nonadecane, cyclopentane, cyclohexane, cycloheptane, cyclooctane, methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof.

(Compound B).

The compound B is an aromatic hydrocarbon compound which may be substituted with an aliphatic hydrocarbon group. The compound B is preferably a C5-20 hydrocarbon compound. Specific examples of the compound B include: benzene, toluene, ethylbenzene, butylbenzene, pentylbenzene, hexylbenzene, octylbenzene, biphenyl, terphenyl, diphenylethane, (methylphenyl)phenylethane, dimethylbiphenyl, benzyltoluene, dibenzyltoluene, naphthalene, methylnaphthalene, ethylnaphthalene, butylnaphthalene and structural isomers thereof.

(Compound C)

The compound C is a compound having either an ether bond or a sulfide bond, and an aliphatic hydrocarbon group, the compound being formed by binding the same kind or different kind of aliphatic hydrocarbon compounds via an ether bond or a sulfide bond. The compound C is preferably a C2-20 compound. Specific examples of the compound C include: ethers in which hydrocarbon compounds are bonded via an ether bond, such as ethyl ether, butyl ether, octyl ether, nonyl ether, decyl ether, methylethyl ether, methylbutyl ether, methyloctyl ether, methylnonyl ether, methyldecyl ether, ethylbutyl ether, ethyloctyl ether, ethylnonyl ether, ethyldecyl ether, butyloctyl ether, butylnonyl ether, butyldecyl ether, octylnonyl ether, octyldecyl ether, dicyclopentyl ether, dicyclohexyl ether, dicyclooctyl ether, cyclohexylethyl ether, cyclohexylbutyl ether, cyclohexyloctyl ether, cyclohexylnonyl ether, cyclohexyldecyl ether, tetraethylene glycol dimethyl ether and structural isomers thereof; and sulfides in which hydrocarbon compounds are bonded via a sulfide bond, such as methyl sulfide, ethyl sulfide, butyl sulfide, octyl sulfide, nonyl sulfide, decyl sulfide, methylethyl sulfide, methylbutyl sulfide, methyloctyl sulfide, methylnonyl sulfide, methyldecyl sulfide, ethylbutyl sulfide, ethyloctyl sulfide, ethylnonyl sulfide, ethyldecyl sulfide, butyloctyl sulfide, butylnonyl sulfide, butyldecyl sulfide, octylnonyl sulfide, octyldecyl sulfide, dicyclopentyl sulfide, dicyclohexyl sulfide, dicyclooctyl sulfide, cyclohexylethyl sulfide, cyclohexylbutyl sulfide, cyclohexyloctyl sulfide, cyclohexylnonyl sulfide, cyclohexyldecyl sulfide and structural isomers thereof. Among these, a C2-20 alkylether or alkyl sulfide is preferable.

(Compound D)

The compound D is a compound which has either an ether bond or a sulfide bond, and an aromatic hydrocarbon group, and is formed by binding the same kind or different kind of aromatic hydrocarbon compounds via an either ether bond or a sulfide bond. The compound D is preferably a C2-20 compound. Specific examples of the compound D include: aromatic ethers in which aromatic hydrocarbon compounds are bonded via an ether bond, such as diphenyl ether, (methylphenyl)-phenyl ether, (ethylphenyl)-phenyl ether, (butylphenyl)-phenyl ether, (hexylphenyl)-phenyl ether, (methylphenyl)ether, (ethylphenyl)ether, (butylphenyl) ether, (hexylphenyl)ether, dibenzylether, di(methylbenzyl) ether, di(ethylbenzyl)ether, di(butylbenzyl)ether, di(pentylbenzyl)ether, di(hexylbenzyl)ether, di(octylbenzyl)ether, and structural isomers thereof; and aromatic sulfides in which aromatic hydrocarbon compound are bonded via a sulfide bond, such as diphenyl sulfide, (methylphenyl)-phenyl sulfide, (ethylphenyl)-phenyl sulfide, (butylphenyl)-phenyl sulfide, (hexylphenyl)-phenyl sulfide, (methylphenyl)sulfide, (ethylphenyl)sulfide, (butylphenyl)sulfide, (hexylphenyl)sulfide, di(methylbenzyl)sulfide, di(ethylbenzyl)sulfide, di(butylbenzyl)sulfide, di(pentylbenzyl)sulfide, di(hexylbenzyl)sulfide, di(octylbenzyl)sulfide, diphenyl sulfide, dibenzyl sulfide, and structural isomers thereof. Among these, diphenyl ether is preferable.

(Compound E)

The compound E is a compound having either an ether bond or a sulfide bond, and both an aliphatic hydrocarbon group and an aromatic hydrocarbon group. The compound E is preferably a C7-20 compound. Specific examples of the compound E include: phenyl-methyl-ether, phenyl-ethyl-ether, phenyl-butyl-ether, phenyl-octyl-ether, phenyl-nonyl-ether, phenyl-decyl-ether, benzyl-ethyl-ether, benzyl-butyl-ether, benzyl-octyl-ether, benzyl-nonyl-ether, benzyl-decyl-ether, (methylphenyl)ethyl ether, (methylphenyl)butyl ether, (methylphenyl)octyl ether, (methylphenyl)nonyl ether, (methylphenyl)decyl ether, (ethylphenyl)ethyl ether, (ethylphenyl)butyl ether, (ethylphenyl)octyl ether, (ethylphenyl) nonyl ether, (ethylphenyl)decyl ether, (butylphenyl)ethyl ether, (butylphenyl)butyl ether, (butylphenyl)octyl ether, (butylphenyl)nonyl ether, (butylphenyl)decyl ether and the structural isomers thereof. Among these, a C1-20 alkylphenyl ether is preferable.

(Compound F)

Compound F is a halide in which at least one hydrogen atom constituting an aliphatic hydrocarbon compound or at least one hydrogen atom constituting an aromatic hydrocarbon compound is substituted with a halogen atom. The compound F is preferably a C2-20 compound. Specific examples of the compound F include chloroethane, chloropropane, chlorobutane, chloropentane, chlorohexane, chloroheptane, chlorooctane, chlorononane, chlorodecane, chlorododecane, chlorotetradecane, chloropentadecane, chlorohexadecane, chlorooctadecane, chlorononadecane, chlorocyclopentane, chlorocyclohexane, chlorocycloheptane, chlorocyclooctane, chloromethylcyclopentane, chloroethylcyclopentane, chloromethylcyclohexane, chloroethylcyclohexane, chloropropylcyclohexane, chlorobutylcyclohexane, chloropentylcyclohexane, chlorohexylcyclohexane, chlorodimethylcyclohexane, chlorodiethylcyclohexane, chlorodibutylcyclohexane, chlorobenzene, chloromethylbenzene, chloroethylbenzene, chlorobutylbenzene, chloropentylbenzene, chlorohexylbenzene, chlorooctylbenzene, chlorobiphenyl, chloroterphenyl, chlorodiphenylethane, chloro(methylphenyl)phenylethane, chlorodimethylbiphenyl, chlorobenzyltoluene, chloronaphthalene, chloromethylnaphthalene, chloroethylnaphthalene, chlorobutylnaphthalene, dichloroethane, dichloropropane, dichlorobutane, dichloropentane, dichlorohexane, dichloroheptane, dichlorooctane, dichlorononane, dichlorodecane, dichlorododecane, dichlorotetradecane, dichloropentadecane, dichlorohexadecane, dichlorooctadecane, dichlorononadecane, dichlorocyclopentane, dichlorocyclohexane, dichlorocycloheptane, dichlorocyclooctane, dichloromethylcyclopentane, dichloroethyl cyclopentane, dichloromethyl cyclohexane, dichloroethyl cyclohexane, dichloropropyl cyclohexane, dichlorobutyl cyclohexane, dichloropentyl cyclohexane, dichlorohexyl cyclohexane, dichlorodimethyl cyclohexane, dichlorodiethyl cyclohexane, dichlorodibutyl cyclohexane, dichlorobenzene, dichloromethylbenzene, dichloroethylbenzene, dichlorobutylbenzene, dichloropentylbenzene, dichlorohexylbenzene, dichlorooctylbenzene, dichlorobiphenyl, dichloroterphenyl, dichlorodiphenylethane, dichloro(methylphenyl)phenylethane, dichlorodimethylbiphenyl, dichlorobenzyltoluene, dichloronaphthalene, dichloromethylnaphthalene, dichloroethylnaphthalene, dichlorobutylnaphthalene, dibromoethane, dibromopropane, dibromobutane, dibromopentane, dibromohexane, dibromoheptane, dibromooctane, dibromononane, dibromodecane, dibromododecane, dibromotetradecane, dibromopentadecane, dibromohexadecane, dibromooctadecane, dibromomononadecane, dibromocyclopentane, dibromocyclohexane, dibromocycloheptane, dibromocyclooctane, dibromomethylcyclopentane, dibromoethylcyclopentane, dibromomethylcyclohexane, dibromoethylcyclohexane, dibromopropylcyclohexane, dibromobutylcyclohexane, dibromopentylcyclohexane, dibromohexylcyclohexane, dibromodimethylcyclohexane, dibromodiethyl cyclohexane, dibromodibutylcyclohexane, dibromobenzene, dibromomethylbenzene, dibromoethylbenzene, dibromobutylbenzene, dibromopentylbenzene, dibromohexylbenzene, dibromooctylbenzene, dibromobiphenyl, dibromoterphenyl, dibromodiphenylethane, dibromo(methylphenyl)phenylethane, dibromodimethylbiphenyl, dibromobenzyltoluene, dibromonaphthalene, dibromomethylnaphthalene, dibromoethylnaphthalene, dibromobutylnaphthalene, difluoroethane, difluoropropane, difluorobutane, difluoropentane, difluorohexane, difluoroheptane, difluorooctane, difluorononane, difluorodecane, difluorododecane, difluorotetradecane, difluoropentadecane, difluorohexadecane, difluorooctadecane, difluorononadecane, difluorocyclopentane, difluorocyclohexane, difluorocycloheptane, difluorocyclooctane, difluoromethylcyclopentane, difluoroethylcyclopentane, difluoromethylcyclohexane, difluoroethylcyclohexane, difluoropropylcyclohexane, difluorobutylcyclohexane, difluoropentylcyclohexane, difluorohexylcyclohexane, difluorodimethylcyclohexane, difluorodiethylcyclohexane, difluorodibutylcyclohexane, difluorobenzene, difluoromethylbenzene, difluoroethylbenzene, difluorobutylbenzene, difluoropentylbenzene, difluorohexylbenzene, difluorooctylbenzene, difluorobiphenyl, difluoroterphenyl, difluorodiphenylethane, difluoro(methylphenyl)phenylethane, difluorodimethylbiphenyl, difluorobenzyltoluene, difluoronaphthalene, difluoromethylnaphthalene, difluoroethylnaphthalene, difluorobutylnaphthalene and structural isomers thereof.

(Compound G)

The compound G is a compound in which a part or all of carbon atoms of the compounds A to E are substituted with silicon atoms. Specific examples of the compound G include tetraethylsilane, tetrabutylsilane, tetrahexylsilane, tetracyclohexylsilane, tetraphenylsilane, dimethyldibutylsilane, dimethyldicyclohexylsilane, dimethyldiphenylsilane, hexamethylcyclotrisiloxane, hexaethylcyclotrisiloxane, hexacyclohexylcyclotrisiloxane, trimethyltricyclohexylcyclotrisiloxane, trimethyltriphenylcyclotrisiloxane, hexaphenylcyclotrisiloxane, octamethylcyclotetrasiloxane, octaethylcyclotetrasiloxane, octacyclohexylcyclotetrasiloxane, tetramethyltetracyclohexylcyclotetrasiloxane, tetramethyltetraphenylcyclotetrasiloxane, octaphenylcyclotetrasiloxane, octamethyltrisiloxane, decamethyltetrasiloxane, tetramethyltetraphenyltrisiloxane, pentamethylpentaphenyltetrasiloxane, and structural isomers thereof. Among these, decamethyltetrasiloxane is preferably used.

Among these, there is a case where compounds having either an ether bond or a sulfide bond, such as the compound C, compound D, or compound E, generate oxides or peroxides depending on conditions. From the viewpoint of thermal stability, the compounds A, B, C, D, E, and G are preferable, and the compounds A, B, and G are more preferable.

The presence of the inert compound makes it possible to further improve the storage stability of the isocyanate composition. That is, the inert compound may be referred to as a quality improving agent, a stabilizer, a viscosity increase inhibitor, a generation inhibitor of gelatinous components, or a chromaticity increase inhibitor, of the difunctional diisocyanate and/or trifunctional or more-functional isocyanate compound.

<Halogen Atom which is not Derived from Halogenated Hydrocarbon>

The isocyanate composition according to the present embodiment may further contain 1.0 ppm by mass to $1.0 \times 10^2$ ppm by mass, based on the isocyanate compound, of halogen atoms which are not derived from a halogenated hydrocarbon.

The phrase "which are not derived from a halogenated hydrocarbon" means that halogen atoms constituting the halogenated hydrocarbon are excluded.

Although the halogen atom is not particularly limited, the halogen atom is preferably chlorine and/or bromine, and preferably at least one selected from the group consisting of chlorine ion, bromine ion, chlorine atom contained in a hydrolyzable chlorine compound, and bromine atom contained in a hydrolyzable bromine compound. The halogenated hydrocarbon is distinguished from a hydrolyzable chlorine compound or a hydrolyzable bromine compound in terms of the absence of hydrolyzability under conditions of ordinary temperature and ordinary pressure. The hydrolyzable chlorine compound and the hydrolyzable bromine compound has a hydrolyzability to generate halogen ions under conditions of ordinary temperature and ordinary pressure. Accordingly, a halogen atom which is not derived from a halogenated hydrocarbon is preferably a hydrolyzable chlorine compound, hydrolyzable bromine compound, chlorine ion, or bromine ion.

Examples of the hydrolyzable chlorine compound include carbamoyl chloride compounds in which a hydrogen chloride is added to an isocyanate group. Examples of the hydrolyzable bromine compound include carbamoyl bromide compounds in which a hydrogen bromide is added to an isocyanate group.

<Sulfuric Acid and/or Sulfuric Acid Ester>

The sulfuric acid ester refers to a compound constituted by an ester bond of an alcohol and a sulfuric acid, and specific examples thereof include: benzenesulfonic acid, vinylsulfonic acid, methanesulfonic acid, p-toluenesulfonic acid, monomethylsulfuric acid, monoethylsulfuric acid, and mono n-propylsulfuric acid In addition, a sulfuric acid may be contained.

<Phosphoric Acid and/or Phosphoric Acid Ester>

The phosphoric acid ester according to the present embodiment refers to an ester formed by dehydration condensation of phosphoric acid and alcohol, and may be a phosphoric acid monoester, a phosphoric acid diester, or a phosphoric acid triester. Specific examples thereof include methyl phosphate, dimethyl phosphate, butyl phosphate, dibutyl phosphate, isodecyl phosphate, diisodecyl phosphate, 2-ethylhexyl phosphate, di-2-ethylhexyl phosphate, lauryl phosphate, dilauryl phosphate, stearyl phosphate, distearyl phosphate, dioleyl phosphate, and phenylphosphonic acid. In addition, a phosphoric acid may be contained. Among these, a C1-15 alkyl phosphate is preferable. In addition, a phosphoric acid may be contained.

<Isocyanate Composition>

The first embodiment of the isocyanate composition is an isocyanate composition containing: a trifunctional or more-functional isocyanate compound; and 1.0 ppm by mass to $1.0 \times 10^4$ ppm by mass, based on the isocyanate compound, of a compound having at least one unsaturated bond excluding unsaturated bonds constituting an aromatic ring, the compound being different from the isocyanate.

The compound having at least one unsaturated bond excluding unsaturated bonds constituting an aromatic ring is a compound of formula (28), a carbonic acid derivative (N-unsubstituted carbamic acid ester, carbonate ester, N-substituted carbamic acid ester), a compound having an UV absorption in an area of decamer or higher isocyanates in a measurement spectrum of gel permeation chromatography, a compound having an isocyanurate group and/or a biuret group, or a compound of formula (1).

The amount of the compound having an unsaturated bond is preferably 1.0 ppm by mass to $1.0 \times 10^4$ ppm by mass, based on the trifunctional or more-functional isocyanate compound constituting the composition. One kind of the unsaturated bond compound may be used alone, or a plurality of kinds thereof may be used in combination.

An unsaturated bond compound as a contaminant tends to cause coloring, because an unsaturated bond of the unsaturated bond compound generally tends to be easily oxidized. However, the unsaturated bond compound according to the present embodiment acts effectively on the isocyanate composition, when stored, to improve the stability of the isocyanate compound without coloring the isocyanate composition.

Although the mechanism by which such effects are exhibited is not apparent, it is presumed that the effects are exhibited by selectively reacting the unsaturated bond compounds with water or oxygen, and thereby suppressing the denaturation reaction of the isocyanate compound caused by water or oxygen. Moreover, in the case of a compound having an unsaturated bond between a carbon atom and an oxygen atom, there are many cases where the tendency of exhibiting the effect becomes large.

In order to suppress the denaturation reaction of the isocyanate compound, the amount of the unsaturated bond compound is preferably increased. On the other hand, there is a case where an excessive amount of the unsaturated bond compound generates coloration caused by the unsaturated bond as described above, and thereby deteriorating the external appearance. Thus, the amount of the unsaturated bond compound according to the present embodiment is 1.0 ppm by mass to $1.0 \times 10^4$ ppm by mass, based on the isocyanate compound, the lower limit of the amount is preferably 3.0 ppm by mass or more, more preferably 5.0 ppm by mass or more, and even more preferably 10 ppm by mass or more, and the upper limit of the amount is preferably $5.0 \times 10^3$ ppm by mass or less, more preferably $3.0 \times 10^3$ ppm by mass or less, and even more preferably $1.0 \times 10^3$ ppm by mass or less.

Among these compounds having an unsaturated bond, a compound having an UV absorption in an area of decamer or higher isocyanates in a measurement spectrum of gel permeation chromatography is preferable. It is presumed that the compound suppresses the denaturation reaction of the isocyanate compound caused by water or oxygen because the compound has a 1-nylon structure having a high reactivity against water or oxygen.

In addition, among these compounds having an unsaturated bond, a compound of formula (1) is also preferably used. It is presumed that an ester group of the compound has a reactivity against water or oxygen, and thereby suppressing the denaturation of the isocyanate group caused by water or oxygen.

In addition, a compound having an isocyanurate group and/or a biuret group is also preferably used.

Thus, the first embodiment of the isocyanate composition according to the present embodiment contains: a trifunctional or more-functional isocyanate compound; and 1.0 ppm by mass to $1.0 \times 10^4$ ppm by mass, based on the isocyanate compound, of the compound having at least one unsaturated bond excluding unsaturated bonds constituting an aromatic ring, the compound being different from the isocyanate, and preferably further contains 1.0 ppm by mass to $1.0 \times 10^4$ ppm by mass, based on the isocyanate compound, of at least one inert compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound not having any double bonds between carbon atoms or between a carbon atom and an oxygen atom excluding unsaturated bonds constituting an aromatic ring.

Among these, compounds having an ether bond or a sulfide bond, such as the compound C, the compound D, or the compound E, may generate an oxide or a peroxide depending conditions. From the viewpoint of thermal stability, the compounds A, B, C, D, E, and G are preferable, and the compounds A, B, and G are more preferable. One kind of the inert compound may be used alone, or a plurality of kinds thereof may be used in combination.

Although the inert compounds generally do not have reactivity against water, oxygen, or the like, and it is quite unlikely that the inert compound acts in the same way as the unsaturated bond compounds, the inventors of the present invention surprisingly found that the isocyanate composition further containing the inert compound also exhibits effects of improving the stability of the isocyanate.

Although the mechanism by which such effects are exhibited is not apparent, the isocyanate compound generally reacts with water or oxygen, the isocyanate composition is stored in a storage container such as an airtight glass container, an 18-litter square can, or a drum can. However, in the case of a usual storage, it is presumed that the undesired viscosity increase of the isocyanate composition and the generation of gelatinous components are induced by the action of water or oxygen infinitesimally contaminated by leaking from an external portion or when the storage container is filled with the isocyanate composition. In contrast, it is presumed that a part of the inert compound infinitesimally existing together in the isocyanate composition according to the present embodiment vaporizes in the storage container, exists as a vapor component in a vapor portion in the storage container, and thereby suppressing the influences of the infinitesimally existing water or oxygen, and exhibits further favorable effects in combination with the compound having an unsaturated bond.

Although the amount of the inert compound is preferably increased in view of the above-mentioned circumstances, there is a case where an excess amount thereof significantly changes properties originally expected to be provided to the isocyanate composition, such as viscosity. Thus, the amount of the inert compound according to the present embodiment is 1.0 ppm by mass to $1.0 \times 10^4$ ppm by mass, the lower limit thereof is preferably 3.0 ppm by mass or more, more preferably 5.0 ppm by mass or more, and even more preferably 10 ppm by mass or more, and the upper limit thereof is preferably $5.0 \times 10^3$ ppm by mass or less, more preferably $3.0 \times 10^3$ ppm by mass or less, and even more preferably $1.0 \times 10^3$ ppm by mass or less. One kind of the inert compound may be used alone, or a plurality of kinds thereof may be used in combination.

The isocyanate composition containing a trifunctional or more-functional isocyanate compound and a compound having an unsaturated bond may further contain a sulfuric acid, a sulfuric acid ester, a phosphoric acid, and/or phosphoric acid ester.

The stability of the isocyanate composition when stored is further improved by further containing a sulfuric acid and/or a sulfuric acid ester. Although the mechanism by which such an effect is exhibited is not apparent, it is presumed that the sulfuric acid and the sulfuric acid ester moderately suppresses the formation of a 1-nylon body structure of the formula (37) in the composition according to the present embodiment, and thereby suppressing gelation of the whole composition caused by an increase in the compound. Thus, it is preferable that the sulfuric acid and/or the sulfuric acid ester be contained in a moderate amount range so as to further improve the stability of the isocyanate. The amount thereof, based on the isocyanate compound, is 1.0 ppm by mass to $1.0 \times 10^3$ ppm by mass, the lower limit of the amount is preferably 3.0 ppm by mass or more, and more preferably 5.0 ppm by mass or more, and the upper limit of the amount is preferably $1.0 \times 10^2$ ppm by mass or less.

The isocyanate composition further containing a phosphoric acid and/or a phosphoric acid ester also improves the stability when stored. Although the mechanism by which such an effect is exhibited is not apparent, it is presumed that the phosphoric acid and the phosphoric acid ester moderately suppresses the formation of 1-nylon body structure of the formula (37) in the composition according to the present embodiment in the same way as that of a sulfuric acid and a sulfuric acid ester, and thereby suppressing the gelation of the whole composition caused by the increase in the compound. Thus, so as to further improve the stability of the isocyanate, the phosphoric acid and/or the phosphoric acid ester is preferably contained in a moderate range of the amount thereof, and the amount, based on the isocyanate compound, is 1.0 ppm by mass to $1.0 \times 10^3$ ppm by mass, the lower limit of the amount is preferably 3.0 ppm by mass or more, and even more preferably 5.0 ppm by mass or more, and the upper limit of the amount is more preferably $1.0 \times 10^1$ ppm by mass or less.

The isocyanate composition containing: a trifunctional or more-functional isocyanate compound; and at least one unsaturated bond, according to the first embodiment of the isocyanate composition, preferably further contain a halogen atom which is not derived form a halogenated hydrocarbon (hereinafter, may be referred to as simply halogen atom). The amount of the halogen atom is preferably 1.0 ppm by mass to $1.0 \times 10^2$ ppm by mass.

In the isocyanate composition according to the present embodiment, a halogen atom is contained in various form. The halogen atom is preferably chlorine and/or bromine, and at least one selected from the group consisting of chlorine ion, bromine ion, chlorine atom contained in a hydrolyzable chlorine compound, and bromine atom contained in a hydrolyzable bromine compound. The total amount of these chlorine atom and bromine atom may be adjusted to be fallen within the above-mentioned range. The trifunctional or more-functional isocyanate compound and a compound containing a halogen atom may be charged such that the charged amount thereof be fallen within the above-mentioned range, the amount of chlorine atom and bromine atom in the composition may be determined by inductively coupled plasma (ICP), the amount of chlorine ion and bromine ion therein may be determined by anion chromatography, or the hydrolyzable chlorine may be measured in accordance with a test method of hydrolyzable chlorine described in appendix 3 of JIS K-1556 (2000).

The isocyanate composition containing a halogen atom improves the stability when stored. Although the mechanism by which such an effect is exhibited is not apparent, it is presumed that a halogen atom traps oxygen or water, which deteriorates the stability of the trifunctional or more-functional isocyanate compound, and thereby exhibiting the effect of improving the stability of the trifunctional or more-functional isocyanate compound.

Thus, the amount of halogen atom is preferably increased so as to further improve the stability of the isocyanate, whilst an excessive amount of the halogen atom generates coloration caused by the halogen atom, and may deteriorate the external appearance when used as a coating raw material, for example. Accordingly, the amount of halogen atom in the isocyanate composition according to the present embodiment, based on the isocyanate compound, is 1.0 ppm by mass to $1.0 \times 10^2$ ppm by mass, the lower limit of the amount is preferably 3.0 ppm by mass or more, and more preferably 5.0 ppm by mass or more, and the upper limit of the amount is more preferably $5.0 \times 10^1$ ppm by mass or less.

Since the effects exhibited by containing a halogen atom which is not derived from a halogenated hydrocarbon are also exhibited when the isocyanate composition containing: a trifunctional or more-functional isocyanate compound; and a compound having an unsaturated bond; and any of an inert compound, a sulfuric acid, a sulfuric acid ester, a phosphoric acid, and a phosphoric acid ester, further contains a halogen atom which is not derived from a halogenated hydrocarbon, the isocyanate composition containing: a trifunctional or more-functional isocyanate compound; and a compound having an unsaturated bond; and any of an inert compound, a sulfuric acid, a sulfuric acid ester, a phosphoric acid, and a phosphoric acid ester, and further containing a halogen atom which is not derived from a halogenated hydrocarbon is one of preferable embodiments. In this case, the halogen atom is contained in the above-mentioned amount in the isocyanate composition, and exhibits the same effects.

The second embodiment of the isocyanate composition contains: a trifunctional or more-functional isocyanate compound; and, based on the isocyanate compound, 1.0 ppm by mass to $1.0 \times 10^3$ ppm by mass of a sulfuric acid and/or a sulfuric acid ester, and/or, 1.0 ppm by mass to $1.0 \times 10^3$ ppm by mass of a phosphoric acid and/or a phosphoric acid ester.

The explanation of the same constitution as the first embodiment may be omitted.

The isocyanate composition containing the sulfuric acid and the sulfuric acid ester improves the stability when stored. Although the mechanism by which such an effect is exhibited is not apparent, it is presumed that the sulfuric acid and the sulfuric acid ester moderately suppresses the formation of the 1-nylon body structure of the formula (37) in the composition according to the present embodiment, and thereby suppressing the gelation of the whole composition caused by the increase in the compound. Thus, in order to further improve the stability of the isocyanate, the sulfuric acid and the sulfuric acid ester are preferably contained in an appropriate amount range, and the amount thereof, based on the isocyanate compound, is 1.0 ppm by mass to $1.0 \times 10^3$ ppm by mass, the lower limit of the amount is preferably 3.0 ppm by mass or more, and more preferably 5.0 ppm by mass or more, and the upper limit of the amount is more preferably $1.0 \times 10^2$ ppm by mass or less.

The isocyanate composition containing a phosphoric acid and a phosphoric acid ester improves the stability when stored. Although the mechanism by which such an effect is exhibited is not apparent, it is presumed that the phosphoric acid and the phosphoric acid ester moderately suppresses the formation of the 1-nylon body structure of the formula (37) in the composition according to the present embodiment in the same way as the sulfuric acid and the sulfuric acid ester, and thereby suppressing the gelation of the whole composition caused by the increase in the compound. Thus, in order to further improve the stability of the isocyanate, the phosphoric acid and the phosphoric acid ester are preferably contained in an appropriate amount range, and the amount thereof, based on the isocyanate compound, is 1.0 ppm by mass to $1.0 \times 10^3$ ppm by mass, the lower limit of the amount is preferably 3.0 ppm by mass or more, and more preferably 5.0 ppm by mass or more, and the upper limit of the amount is more preferably $1.0 \times 10^2$ ppm by mass or less.

The isocyanate composition containing: a trifunctional or more-functional isocyanate compound; and, based on the isocyanate compound, 1.0 ppm by mass to $1.0 \times 10^3$ ppm by mass of a sulfuric acid and/or a sulfuric acid ester, and/or, 1.0 ppm by mass to $1.0 \times 10^3$ ppm by mass of a phosphoric acid and/or a phosphoric acid ester, according to the second embodiment preferably further contains an inert compound, and preferably further contains 1.0 ppm by mass to $1.0 \times 10^4$ ppm by mass, based on the isocyanate compound, of at least one inert compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound containing neither unsaturated bond between carbon atoms nor double bond between a carbon atom and an oxygen atom excluding unsaturated bonds constituting an aromatic ring. The compounds A, B, C, D, E, and G are preferable from the viewpoint of thermal stability, and the compounds A, B and G are preferable in terms that neither oxide nor peroxide is generated. One kind of the inert compound may be used alone, or a plurality of kinds thereof may be used in combination.

The presence of the inert compound which does not have reactivity against water, oxygen, or the like further improves the stability of an isocyanate in the isocyanate composition according to the present embodiment.

It is presumed that such an effect is exhibited by vaporizing a part of the inert compound infinitesimally existing together in the storage container to infinitesimally exist as a vapor component, and thereby suppressing the viscosity increase or generation of gelatinous components caused by infinitesimally existing water or oxygen.

Although the amount of the inert compound is preferably increased in view of the above-mentioned circumstances, there is a case where an excess amount thereof significantly changes properties originally expected to be provided to the isocyanate composition, such as viscosity. Thus, the amount of the inert compound according to the present embodiment is 1.0 ppm by mass to $1.0 \times 10^4$ ppm by mass, the lower limit thereof is preferably 3.0 ppm by mass or more, more preferably 5.0 ppm by mass or more, and even more preferably 10 ppm by mass or more, and the upper limit thereof is preferably $5.0 \times 10^3$ ppm by mass or less, more preferably $3.0 \times 10^3$ ppm by mass or less, and even more preferably $1.0 \times 10^3$ ppm by mass or less. One kind of the inert compound may be used alone, or a plurality of kinds thereof may be used in combination.

In addition, it is preferable that the isocyanate composition containing: a trifunctional or more-functional isocyanate compound; and, based on the isocyanate compound, 1.0 ppm by mass to $1.0 \times 10^3$ ppm by mass of a sulfuric acid and/or a sulfuric acid ester, and/or, 1.0 ppm by mass to $1.0 \times 10^3$ ppm by mass of a phosphoric acid and/or a phosphoric acid ester further contain a halogen atom which is not derived from a halogenated hydrocarbon (hereinafter, may be referred to as a halogen atom simply). The amount of the halogen atom is preferably 1.0 ppm by mass to $1.0 \times 10^2$ ppm by mass.

In the isocyanate composition according to the present embodiment, a halogen atom is contained in various form. The halogen atom is preferably chlorine and/or bromine, and at least one selected from the group consisting of chlorine ion, bromine ion, chlorine atom contained in a hydrolyzable chlorine compound, and bromine atom contained in a hydrolyzable bromine compound. The total amount of these chlorine atom and bromine atom may be adjusted to be fallen within the above-mentioned range. The trifunctional or more-functional isocyanate compound and a compound containing a halogen atom may be charged such that the charged amount thereof be fallen within the above-mentioned range, the amount of chlorine atom and bromine atom in the composition may be determined by inductively coupled plasma (ICP), the amount of chlorine ion and bromine ion therein may be determined by anion chromatography, or the hydrolyzable chlorine may be measured in accordance with a test method of hydrolyzable chlorine described in appendix 3 of JIS K-1556 (2000).

The isocyanate composition containing a halogen atom improves the stability when stored. Although the mechanism by which such an effect is exhibited is not apparent, it is presumed that a halogen atom traps oxygen or water, which deteriorates the stability of the trifunctional or more-functional isocyanate compound, and thereby exhibiting the effect of improving the stability of the trifunctional or more-functional isocyanate compound.

Thus, the amount of halogen atoms is preferably increased so as to further improve the stability of the isocyanate, whilst an excessive amount of halogen atoms generates coloration caused by the halogen atom, and may deteriorate the external appearance when used as a coating raw material, for example. Accordingly, the amount of halogen atoms in the isocyanate composition according to the present embodiment, based on the isocyanate compound, is 1.0 ppm by mass to $1.0 \times 10^3$ ppm by mass, the lower limit of the amount is preferably 3.0 ppm by mass or more, and more preferably 5.0 ppm by mass or more, and the upper limit of the amount is more preferably $5.0 \times 10^1$ ppm by mass or less.

The third embodiment of the isocyanate composition contains: a difunctional or more-functional isocyanate compound; and 1.0 ppm by mass to $1.0 \times 10^4$ ppm, based on the isocyanate compound, of a compound having at least one unsaturated bond, and the compound having at least one unsaturated bond is a compound having an UV absorption in an area of decamer or higher isocyanates in a measurement spectrum of gel permeation chromatography.

The explanation of the same constitution as that of the first or second embodiment may be omitted.

Although oxidation of an unsaturated bond easily causes coloration in general, the unsaturated bond compound in the isocyanate composition according to the present embodiment acts effectively on the isocyanate composition, when stored, to improve the stability of the isocyanate compound without coloring the isocyanate composition.

It is presumed that such effects are exhibited by selectively reacting the unsaturated bond compounds with water or oxygen, and thereby suppressing the denaturation reaction of the isocyanate compound caused by water or oxygen. Moreover, in the case of a compound having an unsaturated bond between a carbon atom and an oxygen atom, there are many cases where the tendency of exhibiting the effect becomes large.

In order to suppress the denaturation reaction of the isocyanate compound, the amount of the unsaturated bond compound is preferably increased. On the other hand, there is a case where an excessive amount of the unsaturated bond compound generates coloration caused by the unsaturated bond as described above, and thereby deteriorating the external appearance. Thus, the amount of the unsaturated bond compound according to the present embodiment is 1.0 ppm by mass to $1.0 \times 10^4$ ppm, based on the isocyanate compound, the lower limit of the amount is preferably 3.0 ppm by mass or more, more preferably 5.0 ppm by mass or more, and even more preferably 10 ppm by mass or more, and the upper limit of the amount is preferably, $5.0 \times 10^3$ ppm by mass or less, more preferably $3.0 \times 10^3$ ppm by mass or less, and even more preferably $1.0 \times 10^3$ ppm by mass or less.

Thus, the isocyanate composition according to the present embodiment contains: a difunctional or more-functional isocyanate compound; and 1.0 ppm by mass to $1.0 \times 10^4$ ppm, based on the isocyanate compound, of a compound having at least one unsaturated bond, and the compound having at least one unsaturated bond is a compound having an UV absorption in an area of decamer or higher isocyanates in a measurement spectrum of gel permeation chromatography. The isocyanate composition preferably further contain 1.0 ppm by mass to $1.0 \times 10^4$ ppm, based on the isocyanate compound, of at least one inert compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound not having unsaturated bonds between carbon atoms and double bonds between a carbon atom and an oxygen atom excepting unsaturated bonds constituting an aromatic ring. Among these, the compounds A, B, C, D, E, and G are preferable from the viewpoint of thermal stability, and the compounds A, B and G are preferable in terms that neither oxide nor peroxide is generated. One kind of the inert compound may be used alone, or a plurality of kinds thereof may be used in combination.

Although the inert compound generally does not have reactivity against water, oxygen, or the like, the presence of the inert compound further improves the stability of an isocyanate in the isocyanate composition according to the present embodiment.

It is presumed that such an effect is exhibited by vaporizing a part of the inert compound infinitesimally existing together in the storage container to exist as a vapor component, and thereby suppressing the effects of infinitesimally existing water or oxygen to suppress the viscosity increase or generation of gelatinous components.

Although the amount of the inert compound is preferably increased in view of the above-mentioned circumstances, there is a case where an excess amount thereof significantly changes properties originally expected to be provided to the isocyanate composition, such as viscosity. Thus, the amount of the inert compound according to the present embodiment is 1.0 ppm by mass to $1.0 \times 10^4$ ppm by mass, the lower limit thereof is preferably 3.0 ppm by mass or more, more preferably 5.0 ppm by mass or more, and even more preferably 10 ppm by mass or more, and the upper limit thereof is preferably $5.0 \times 10^3$ ppm by mass or less, more preferably $3.0 \times 10^3$ ppm by mass or less, and even more preferably $1.0 \times 10^3$ ppm by mass or less. One kind of the inert compound may be used alone, or a plurality of kinds thereof may be used in combination.

In addition, the isocyanate composition containing: a difunctional or more-functional isocyanate compound; and a compound having an unsaturated bond preferably further contains a sulfuric acid, a sulfuric acid ester, a phosphoric acid, and/or, a phosphoric acid ester.

The stability of the isocyanate composition when stored is further improved by further containing a sulfuric acid and/or a sulfuric acid ester. Although the mechanism by which such an effect is exhibited is not apparent, it is presumed that the sulfuric acid and the sulfuric acid ester moderately suppresses the formation of a 1-nylon body structure of the formula (37) in the composition according to the present embodiment, and thereby suppressing gelation of the whole composition caused by an increase in the compound. Thus, it is preferable that the sulfuric acid and/or the sulfuric acid ester be contained in a moderate amount range so as to further improve the stability of the isocyanate. The amount thereof, based on the isocyanate compound, is 1.0 ppm by mass to $1.0 \times 10^3$ ppm by mass, the lower limit of the amount is preferably 3.0 ppm by mass or more, and more preferably 5.0 ppm by mass or more, and the upper limit of the amount is preferably $1.0 \times 10^2$ ppm by mass or less.

The isocyanate composition further containing a phosphoric acid and/or a phosphoric acid ester also further improves the stability when stored. Although the mechanism by which such an effect is exhibited is not apparent, it is presumed that the phosphoric acid and the phosphoric acid ester moderately suppresses the formation of 1-nylon body structure of the formula (37) in the composition according to the present embodiment in the same way as that of a sulfuric acid and a sulfuric acid ester, and thereby suppressing the gelation of the whole composition caused by the increase in the compound. Thus, so as to further improve the stability of the isocyanate, the phosphoric acid and/or the phosphoric acid ester is preferably contained in a moderate range of the amount thereof, and the amount, based on the isocyanate compound, is 1.0 ppm by mass to $1.0 \times 10^3$ ppm by mass, the lower limit of the amount is preferably 3.0 ppm by mass or more, and even more preferably 5.0 ppm by mass or more, and the upper limit of the amount is more preferably $1.0 \times 10^1$ ppm by mass or less.

The isocyanate composition according to the present embodiment also preferably further contains a halogen atom which is not derived from a halogenated hydrocarbon (hereinafter, may be referred to as halogen atom, simply). The amount of the halogen atom is preferably 1.0 ppm by mass to $1.0 \times 10^2$ ppm by mass.

In the isocyanate composition according to the present embodiment, a halogen atom is contained in various form, as described above. The halogen atom is preferably chlorine and/or bromine, and at least one selected from the group consisting of chlorine ion, bromine ion, chlorine atom contained in a hydrolyzable chlorine compound, and bromine atom contained in a hydrolyzable bromine compound. The total amount of these chlorine atom and bromine atom may be adjusted to be fallen within the above-mentioned range. The difunctional or more-functional isocyanate compound and a compound containing a halogen atom may be charged such that the charged amount thereof be fallen within the above-mentioned range, the amount of chlorine atom and bromine atom in the composition may be determined by inductively coupled plasma (ICP), the amount of chlorine ion and bromine ion therein may be determined by anion chromatography, or the hydrolyzable chlorine may be measured in accordance with a test method of hydrolyzable chlorine described in appendix 3 of JIS K-1556 (2000).

The isocyanate composition containing a halogen atom improves the stability when stored. Although the mechanism by which such an effect is exhibited is not apparent, it is presumed that a halogen atom traps oxygen or water, which deteriorates the stability of the difunctional or more-functional isocyanate compound, and thereby exhibiting the effect of improving the stability of the difunctional or more-functional isocyanate compound.

Thus, the amount of halogen atom is preferably increased so as to further improve the stability of the isocyanate, whilst an excessive amount of the halogen atom generates coloration caused by the halogen atom, and may deteriorate the external appearance when used as a coating raw material, for example. Accordingly, the amount of halogen atom in the isocyanate composition according to the present embodiment, based on the isocyanate compound, is 1.0 ppm by mass to $1.0 \times 10^2$ ppm by mass, the lower limit of the amount is preferably 3.0 ppm by mass or more, and more preferably 5.0 ppm by mass or more, and the upper limit of the amount is more preferably $5.0 \times 10^1$ ppm by mass or less.

Since the effects exhibited by containing a halogen atom which is not derived from a halogenated hydrocarbon are also exhibited when the isocyanate composition containing: a difunctional or more-functional isocyanate compound; and a compound having an unsaturated bond; and any of an inert compound, a sulfuric acid, a sulfuric acid ester, a phosphoric acid, and a phosphoric acid ester, further contains a halogen atom which is not derived from a halogenated hydrocarbon, the isocyanate composition containing: a difunctional or more-functional isocyanate compound; and a compound having an unsaturated bond; and any of an inert compound, a sulfuric acid, a sulfuric acid ester, a phosphoric acid, and a phosphoric acid ester, and further containing a halogen atom which is not derived from a halogenated hydrocarbon is one of preferable embodiments. In this case, the halogen atom is contained in the above-mentioned amount in the isocyanate composition, and exhibits the same effects.

<Method for Producing Isocyanate Composition>

The isocyanate composition according to the present embodiment may be produced by appropriately mixing an isocyanate compound, a compound having an unsaturated bond, an inert compound, a halogen atom which is not derived from a halogenated hydrocarbon, sulfuric acid, sulfuric acid ester, a phosphoric acid, and, a phosphoric acid ester.

The isocyanate compound may be produced by a conventionally-known method. For example, a corresponding organic primary amine and a phosgene are reacted, and hydrogen chloride is eliminated to produce an isocyanate compound. The reaction of the organic primary amine and the phosgene may be conducted in a solvent or a vapor phase.

The isocyanate composition according to the present embodiment may be produced by appropriately mixing the isocyanate compound obtained by subjecting the isocyanate compound obtained by the conventionally-known method, as described above, to a purification step by a conventionally-known method, with a compound having an unsaturated bond, an inert compound, a halogen atom which is not derived from a halogenated hydrocarbon, a sulfuric acid, a sulfuric acid ester, a phosphoric acid, and, a phosphoric acid ester. The compound having an unsaturated bond, the inert compound, the halogen atom which is not derived from a halogenated hydrocarbon, the sulfuric acid, the sulfuric acid ester, the phosphoric acid, and, the phosphoric acid ester, may be previously added to obtain the isocyanate composition according to the present embodiment in the production step of the isocyanate compound, or may be added to obtain the isocyanate composition according to the present embodiment after the isocyanate compound is obtained.

A compound having an UV absorption at an area of decamer or higher isocyanates in a measurement spectrum of gel permeation chromatography is produced, for example, by reacting an isocyanate compound having at least one isocyanate group in a molecule thereof in the presence of a catalyst, followed by adding a terminating agent thereto to stop the polymerization reaction. As the catalyst, the same catalyst as that used in the isocyanurate-forming reaction described below may be used. Although the amount of the catalyst to be used depends on the kind of the used compound, the amount may be $1.0 \times 10^4$ parts by mass to 1.0 part by mass, relative to 100 parts by mass of the isocyanate compound. The upper limit of the amount of the catalyst to be used is preferably $5.0 \times 10^{-1}$ parts by mass or less, more preferably $1.0 \times 10^{-1}$ parts by mass or less, and even more preferably $2.0 \times 10^{-2}$ parts by mass or less, from the viewpoint of the suppressibility of coloration or discoloration of the resultant products and reaction control. The lower limit of the amount of the catalyst to be used is preferably $1.0 \times 10^{-3}$ parts by mass or more, and more preferably $2.0 \times 10^{-3}$ parts by mass or more, from the viewpoint of reactivity.

As the terminating agent, the same terminating agent as that used in the isocyanurate-forming reaction described below may be used. Although the amount of the terminating agent to be used may be appropriately selected depending on the amount of the used catalyst or the kind of the used compound, the amount is preferably at least 1 equivalent, relative to the amount of the used catalyst.

The temperature at which polymerization reaction of the isocyanate compound is conducted in the presence of a catalyst is preferably −20° C. to 60° C. There is a tendency that the isocyanurate-forming reaction easily proceeds in association with the increase in the reaction temperature, and therefore the reaction temperature is preferably low so as to obtain a 1-nylon body structure. On the other hand, the polymerization reaction of the isocyanate compound proceeds excessively slowly at an excessively low reaction temperature, and therefore the reaction temperature is more preferably −10° C. to 50° C., and even more preferably 0° C. to 40° C.

Although the polymerization of the isocyanate compound is conducted in the presence or absence of a solvent, the polymerization is preferably conducted in the presence of a solvent from the viewpoint of easiness in reaction control and operation.

As the solvent, a solvent which is inert to the isocyanate compound to be used, and can dissolve both a raw isocyanate compound and a resultant polymer. Specifically, as the solvent, acetate esters, such as ethyl acetate, butyl acetate, or amyl acetate; aromatic hydrocarbons such as benzene, toluene, xylene, or monochlorobenzene, or the like may be used alone or in combination.

The progress of polymerization may be tracked by appropriately sampling the reaction liquid and then conducting gel permeation chromatography measurement, and the reaction may be stopped by adding a terminating agent to the reaction liquid when a peak is confirmed at an area of desired molecular weight. In the case where the isocyanurate-forming reaction is conducted in the absence of the solvent, an unreacted isocyanate compound serves as a solvent by making the conversion rate be 50% or less to dissolve the resultant polymer therein.

The thus produced compound having an UV absorption at an area of decamer of isocyanate in a measurement spectrum of gel permeation chromatography may be collected by removing the unreacted isocyanate compound and the solvent from the reaction liquid after the end of the reaction, or the reaction liquid may be used directly to produce an isocyanate composition according to the present embodiment. The method for collecting the isocyanurate compound is not particularly limited, and examples thereof include a method in which an unreacted polyisocyanate and a solvent is removed by conducting distillation purification. The removal process is preferably conducted at a low temperature, and using, for example, an apparatus which has a large evaporation area for liquid and exhibits a favorable evaporation efficiency, such as falling thin-film evaporator, thin-film evaporation apparatus, or molecular distillation apparatus.

Regarding to the compound containing an isocyanurate group and/or a biuret group, a compound containing an isocyanurate group may be produced by the same method as described in <method for producing an isocyanate polymer> described below.

The compound having a biuret group may be produced by allowing the reaction to proceed using, for example, water, monovalent tertiary alcohol, formic acid, hydrogen sulfide, organic primary monoamine, or organic primary diamine, as a biuret-forming agent, at a reaction temperature of 70° C. to 200° C., for 10 minutes to 24 hours, followed by, after the end of the reaction, separating unreacted polyisocyanates and a solvent from a composition containing an isocyanate polymer by conducting treatment such as a thin film distillation method or a solvent extraction method. The same solvent as that of the <method for producing isocyanate polymer> described below may be used in the biuret-forming reaction.

<Method for Producing Isocyanate Polymer>

In one embodiment, the present invention provides a method for producing an isocyanate polymer, containing a step in which the isocyanate compound contained in the isocyanate composition is reacted. Hereinafter, the production method according to the present embodiment will be explained. Although the isocyanurate-forming reaction will be mainly explained, conventional-known reactions such as iminooxadiazinedione-forming reaction or uretdione-forming reaction may be used depending on used catalysts or reaction conditions, as described below.

The isocyanurate-forming reaction is preferably conducted in the presence of an isocyanurate-forming catalyst. As the isocyanurate-forming catalyst, basic catalysts are generally preferable, for example, and specific examples thereof include the following compounds (i) to (viii).

(i) Hydroxides or organic acid salts (such as acetic acid salts, butyric acid salts, or decanoic acid salts) of tetraalkyl ammonium (such as tetramethylammonium or tetraethylammonium).

(ii) Hydroxide or organic acid salts (such as acetic acid salts, butyric acid salts, or decanoic acid salts) of trialkyl hydroxy alkyl ammonium (such as trimethyl hydroxypropyl ammonium, trimethyl hydroxyethyl ammonium, triethyl hydroxypropyl ammonium, or triethyl hydroxyethyl ammonium).

(iii) Metal salts (such as tin salts, zinc salts, lead salts, sodium salts, or potassium salts) of alkylcarboxylic acids such as acetic acid, capric acid, octylic acid, or myristic acid.

(iv) Alkoxides of metals such as sodium or potassium.

(V) Aminosilyl group-containing compounds (such as hexamethyldisilazane).

(vi) Phosphorus-based compounds such as tributylphosphine.

(vii) Fluorine compounds or hydrogen polyfluoride compounds (such as tetraalkyl ammonium fluorides such as tetramethyl ammonium fluoride hydrate, or tetraethyl ammonium fluoride).

(viii) Compounds constituted by compounds having a structure of the following formula (40) or formula (41) (such as 3,3,3-trifluoropropionic acid; 3,3,4,4,4-pentafluorobutanoic acid; 3,3,4,4,5,5,5-heptafluoropentanoic acid; or 3,3-difluoropropa-2-enoic acid) and either quaternary ammonium ions or quaternary phosphonium ions.

$$R^{22}=CR'-C(=O)O- \quad (40)$$

$$R^{23}-CR'_2-C(=O)O- \quad (41)$$

In the formulae (40) and (41), $R^{22}$ and $R^{23}$ each independently represent a C1-30 perfluoroalkyl group, each R' independently represents a group selected from the group consisting of a hydrogen atom, a C1-20 alkyl group, and an aromatic group, and $R^{22}$, $R^{23}$, and R' may contain a hetero atom.

In the formulae (40) and (41), $R^{22}$ and $R^{23}$ may each independently represent a linear, branched, or cyclic saturated perfluoroalkyl group or unsaturated perfluoroalkyl group.

Among these, the catalyst (i) or (ii) is preferable as the isocyanurate-forming catalyst from the viewpoint of catalyst efficiency and selectivity of isocyanurate-forming reaction. In addition, the catalyst (vi) is preferably used to form an uretdione structure (the structure of formula (7)) at a high ratio. In addition, the catalyst (vii) or the catalyst (viii) is preferably used to form an iminooxadiazine dione structure (the structure of formula (5)) at a high ratio.

Although the amount of the isocyanurate-forming catalyst to be added to the reaction system of the isocyanurate-forming reaction may be appropriately varied depending on the kind of the used catalyst or the concentration of other components in the reaction system, the amount, relative to 100 parts by mass of the isocyanate compound, may be $1.0 \times 10^4$ parts by mass to 1.0 parts by mass. The upper limit of the used amount of the isocyanurate-forming catalyst is preferably $5.0 \times 10^{-1}$ parts by mass or less, more preferably $1.0×10^{-1}$ parts by mass or less, and even more preferably $2.0×10^{-2}$ parts by mass or less, from the viewpoint of suppressibility of coloring or discoloration or the resultant product and the reaction control. The lower limit of the used amount of the isocyanurate-forming catalyst is more preferably $1.0×10^{-3}$ parts by mass or more, and even more preferably $2.0×10^{-3}$ parts by mass or more, from the viewpoint of reactivity.

The above-mentioned isocyanurate-forming catalyst may simultaneously serve as an allophanate-forming catalyst. Thus, it is possible to allow the isocyanurate-forming reaction and the allophanate-forming reaction to proceed simultaneously by adding a hydroxy group-containing compound before or during the isocyanurate-forming reaction.

The hydroxy group-containing compound is preferably a compound having one or two hydroxy groups in a molecule constituted only by carbon, hydrogen and oxygen, and even more preferably a compound having only one hydroxy group. Specific examples of the compound having one hydroxy group include methyl alcohol, ethyl alcohol, propyl alcohol, butyl alcohol, pentyl alcohol, hexyl alcohol, heptyl alcohol, octyl alcohol, and nonyl alcohol, examples of the compound having two hydroxy groups include ethylene glycol, 1,3-butanediol, 1,4-butanediol, neopentyl glycol, and 2-ethyl hexanediol, and two kinds or more may be used together.

Although the reaction temperature of the isocyanurate-forming reaction is not particularly limited, the reaction temperature is preferably 0° C. to 200° C. In the case where the reaction temperature is less than 0° C., the reaction rate is small, which is not practical. In the case where the reaction temperature exceeds 200° C., the side reaction or excessive coloration of the resultant product tends to easily occur. Among the range, the lower limit of the reaction temperature is more preferably 40° C., even more preferably 50° C., and particularly preferably 60° C., from the viewpoint of the reaction rate. The upper limit of the reaction temperature is more preferably 150° C., even more preferably 120° C., and particularly preferably 110° C., from the viewpoint of the coloration of the resultant product.

The reaction time of the isocyanurate-forming reaction is not particularly limited, and the reaction time may be within a range of 10 seconds to 24 hours.

Examples of a confirmation method of the terminal point of the isocyanurate-forming reaction include: a method for measuring the content rate of the isocyanate group in the reaction mixture (NCO %); a method for measuring a refractive index; and a method in which the reaction mixture is subjected to gel permeation chromatography measurement. The method for measuring the amount of isocyanate groups (NCO %) in the reaction mixture will be described below.

In the case where the isocyanurate-forming reaction excessively proceeds, the viscosity of the resultant product is increased, the amount proportion of the isocyanurate compound is increased, and a manufactured article having intended physical properties may not be obtained, and therefore, the conversion rate of the reaction (mass proportion of the resultant isocyanate polymer, relative to initial mass of isocyanate compound as a raw material) is preferably limited to 50% or less (more preferably 40% or less, and even more preferably 25% or less). Moreover, from the viewpoint of sufficiently obtaining the yield of the isocyanurate compound, the conversion rate of the reaction is preferably 5% or more, more preferably 10% or more, and more preferably 15% or more.

In the production method according to the present embodiment, when the isocyanurate-forming reaction reaches the intended conversion rate, a catalyst-terminating agent is added to the resultant to deactivate the isocyanurate-forming catalyst so that the isocyanurate-forming reaction is terminated. If the catalyst-terminating agent is not added, the isocyanurate-forming reaction further proceeds at a step in which remaining monomers or solvents are distilled away from the isocyanate polymer or when the manufactured article is stored, and thereby causing cases where the viscosity thereof increases and gel components generate. Thus, it is preferable that the isocyanurate-forming catalyst be deactivated by adding the catalyst-terminating agent to the resultant when the intended conversion rate is obtained.

As the catalyst-terminating agent, for example, sulfuric acid, phosphoric acid, acidic phosphate esters, hydrochloric acid, sulfonic acid compounds and the like can be used. In the case where a reaction product of the catalyst-terminating agent and the catalyst is precipitated as a solid, the reaction product is preferably separated by a method such as filtration using a filter or Celite.

Although the isocyanurate-forming reaction may be conducted in the presence or absence of a solvent, the isocyanurate-forming reaction is preferably performed in the presence of a solvent from the viewpoint of easiness in reaction control and operation.

As a solvent available in the isocyanurate-forming reaction, a solvent that is inactive with respect to an isocyanate compound to be used and can dissolve an isocyanate compound used as a raw material and a resultant isocyanurate compound is selected. Specifically, as the solvent, acetate esters such as ethyl acetate, butyl acetate, and amyl acetate; and aromatic hydrocarbons such as benzene, toluene, xylene, and monochlorobenzene may be used alone or in combination.

Moreover, in the case where the isocyanurate-forming reaction is performed in the absence of a solvent, the unreacted polyisocyanate functions as a solvent and can dissolve the resultant isocyanurate compound when the conversion rate is limited to 50% or less. Thus, the conversion rate of the isocyanurate-forming reaction in the absence of a solvent is preferably 5% to 50%, and more preferably 10% to 40%.

After the completion of the isocyanurate-forming reaction, the isocyanurate compound can be collected by removing the unreacted isocyanate compound and the solvent from the reaction system, for example. A removal method is not particularly limited, and the unreacted isocyanate compound and the solvent can be removed by distillation purification, for example. In addition, the removal process is desirably performed at low temperature, and is preferably performed using a device that has a large evaporation surface with respect to liquid and good evaporation efficiency, such as a falling thin-film evaporator, a thin-film evaporation apparatus, or a molecular distillation apparatus.

<Isocyanate Polymer>

The above-mentioned production method is preferably used to produce an isocyanate polymer by polymerizing isocyanate compounds. The isocyanate polymer has: a unit of the following formula (A) or (B); and at least one unit of the following formulae (2) to (8). Nitrogen atoms constituting an isocyanate polymer bond with carbon atoms.

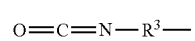
(A)

-continued

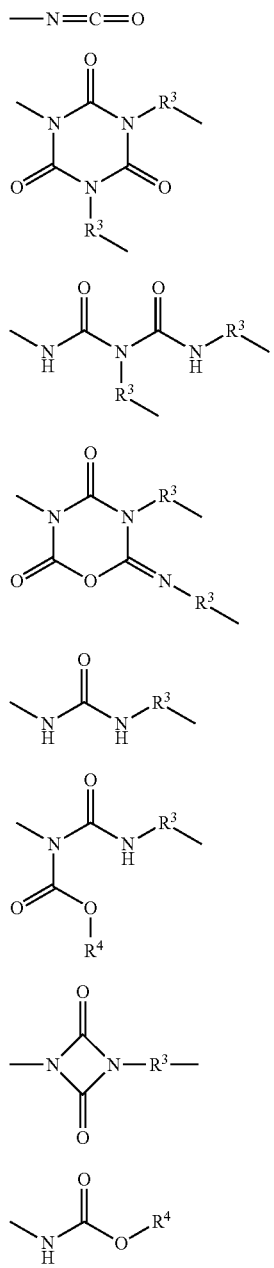

In the formulae (A), (B) and (2) to (8), each $R^3$ independently represents a residual group obtained by removing two isocyanate groups from the isocyanate compound, and each $R^4$ independently represents a monovalent organic group.

In the formulae (6) and (8), $R^4$ depends on a compound used to produce an isocyanate polymer, and, often represents a residual group obtained by removing a hydroxy group (OH group) from the above-mentioned alcohol when the alcohol is used, for example.

Although the structure of the isocyanate polymer according to the present embodiment depends on the used isocyanate compounds, the composition of the isocyanate composition, reaction conditions, or the like, the structure of the following formula (46), (47), (48), or (49) is preferably contained.

In the formulae, $R^3$ represents the same group as $R^3$ in the formulae (A), (B) and (2) to (8), and $R^4$ represents the same group as $R^4$ in the formulae (6) and (8).

The isocyanate compound is not particularly limited, and may be appropriately modified depending on the intended isocyanurate. For example, an aliphatic and/or alicyclic isocyanate is preferably used from the viewpoint of obtaining an isocyanurate polymer preferably available in the application where the weather resistance is required. In addition, an aromatic isocyanate may be selected for the purpose of applying the resultant in the field where the weather resistance is not required.

<Use of Isocyanate Polymer>

A block isocyanate polymer may be manufactured by using a composition including various isocyanate polymers obtained by the above-described production method and blocking a part or all of the isocyanate groups of the isocyanate polymers by a blocking agent.

Moreover, for the purpose of improving water dispersibility, a composition containing a hydrophilic group-modified isocyanate polymer, in which a part of isocyanate groups of various isocyanate polymers obtained by the above-described method is modified by an active hydrogen-containing hydrophilic compound, may also be obtained.

In addition, the isocyanate polymer obtained by the above-mentioned production method may be reacted with a blocking agent and an active hydrogen-containing hydrophilic compound, respectively, when being used as a one-liquid coating material or a cross-linking agent of a coating agent.

As described above, the isocyanate composition exhibits an effect of improving the stability when stored. In addition, an isocyanate polymer may be prepared using the isocyanate composition according to the above-mentioned embodiment. The isocyanate composition or the isocyanate polymer may be appropriately preferably used as a raw material of a coating material, an adhesive agent or the like.

<Method for storing difunctional or more-functional isocyanate compound>

In one embodiment, the present invention provides a method for storing the difunctional or more-functional isocyanate compound. The storing method according to the present embodiment contains: formulating, in the difunctional or more-functional isocyanate compound, 1.0 ppm by mass to $1.0 \times 10^4$ ppm, based on the isocyanate compound, of the compound having at least one unsaturated bond excepting unsaturated bonds constituting an aromatic ring, the compound being different from the isocyanate, a sulfuric acid, a sulfuric acid ester, a phosphoric acid, and/or a phosphoric acid ester.

The storing method according to the present embodiment makes it possible to prevent the isocyanate compound from increasing the viscosity, generating gelatinous components, or increasing the chromaticity, even when the trifunctional or more-functional isocyanate compound is stored for a long period, such as, for 100 days or more, 200 days or more, 300 days or more, or 500 days or more.

EXAMPLES

Although the present invention will be described in more detail below by Examples, the present invention is not limited to the following Examples. The terms "%" and "ppm" described in the Examples mean "% by mass" and "ppm by mass", respectively.

<NCO Amount (NCO %)>

The NCO amount (% by mass) was determined by neutralizing the isocyanate group in the test portion with an excessive amount of 2 N amine and then carrying out back titration with 1 N hydrochloric acid.

<Gel Permeation Chromatography (GPC)>

The measurement method of GPC is described below.
Apparatus used: HLC-8120 (manufactured by Tosoh Corporation)
Column used: TSK GEL Super H1000, TSK GEL Super H2000, TSK GEL Super H3000 (all of these are manufactured by Tosoh Corporation.)
Concentration of test portion: 5 wt/vol % (50 mg of a test portion was dissolved in 1 mL of tetrahydrofuran (THF.))
Carrier: THF
Detection method: Differential refractometer
Outflow: 0.6 mL/min
Column temperature: 30° C.
In producing the calibration curve, polystyrene having a molecular weight of 1,000 to 20,000 was used.

<Liquid Chromatography (LC)>

The measurement method of LC is described below.
Apparatus used: HLC-8120 (manufactured by Tosoh Corporation)
Column used: TSK GEL ODS-5 (manufactured byTosoh Corporation.)
Carrier: acetonitrile/water=50/50 (vol)
Detection method: UV
Outflow: 1.0 mL/min,
Column temperature: 40° C.

<Gas Chromatography (GC)>

Column: The inner diameter was 0.32 mm, the length was 30 m, and the liquid phase film thickness was 1.0 jim (DB-1 manufactured by J&W Scientific, Inc.)
Column temperature: Initial temperature was 50° C., and then the temperature was increased at a rate of 10° C./minute until the final temperature of 300° C. (maintained for 15 minutes at the final temperature).
Injection temperature: 300° C.
Detector temperature: 300° C.
Detector: Flame ionization detector
Carrier gas: Helium
Carrier gas outflow (column): 1.2 mL/minute <NMR Analyzing Method>

Apparatus: JNM-A400 FT-NMR system (manufactured by JEOL LTD.)
Analysis sample: Approximately 0.3 g of a sample solution was accurately weighted, and approximately 0.7 g of deuterochloroform or deuterodimethyl sulfoxide and approximately 0.05 g of tetramethyltin, as an internal standard substance, were added thereto and mixed uniformly to obtain an NMR analysis sample.

<Hazen color number (APHA)>

Numerical values obtained by measurement by a Hazen meter are described as the Hazen color number.

<Measurement of Chlorine Concentration and Bromine Concentration>

A weighted sample was put on a sample board of a combustion pretreatment apparatus, the sample board was moved to a combustion part, the sample was burned by an automatic combustion controller, and the vaporized component was absorbed by an absorbent liquid. The absorbent liquid was injected into an ion chromatograph to determine the amount of the intended component.

Combustion pretreatment apparatus: Automatic combustion controller AQF-100 (manufactured by Mitsubishi Chemical Analytech Co., Ltd.)
Furnace temperature: Inlet 900° C., Outlet 1000° C.
Gas outflow: $Ar/O_2$ 400 mL/minute, $O_2$ 200 mL/minute
Ion chromatograph: ICS-1500 (manufactured by DIONEX)
Guard column: AG 12A
Separation column: AS 12A
Suppressor: ASRS-300
Suppressor current: 50 mA
Eluant: 2.7 mM $Na_2CO_3$, 0.3 mM $NaHCO_3$ Purification Example A1

A sample was supplied into a multi-stage distillation column (selected from structured packing distillation column, random packing distillation column, and plate distillation column). The pressure was controlled at the top portion of the distillation column (absolute pressure), and the heat quantity required for distillation was supplied by a reboiler. After the temperature distribution in the column became stable, a fraction of distillate was removed from a side cut line equipped below the top portion of the column in a height direction. The resultant fraction was analyzed.

Purification Example A2

An isocyanate liquid to be purified was supplied to a falling thin-film-type molecular distillation device (such as MS-300 type manufactured by SHIBATA SCIENTIFIC TECHNOLOGY LTD.), and a vaporized composition component was caught at the surface of a cooling device and then extracted to a collecting device. An inert gas such as nitrogen, argon, or helium was accompanied therewith, as needed.

Purification Example A3

The heat quantity required for distillation was supplied to a falling film type evaporator by a heat medium jacket or a heater, an isocyanate composition to be purified was supplied from an upper portion of the falling film type evaporator, and a vapor phase gas was extracted by countercurrent flow or concurrent flow. An inert gas such as nitrogen, argon, or helium was accompanied therewith, as needed.

Example 1

Preparation of Isocyanate Composition
200 g of 1,3,6-triaminohexane was mixed with 1000 g of o-dichlorobenzene, and a phosgene gas was blown thereinto for 12 hours while heating the mixture at 130° C. In addition, a nitrogen gas was further blown into the resultant to remove phosgene, and o-dichlorobenzene was distilled away at 1 kPa and 120° C. to obtain 190 g of a crude 1,3,6-triisocyanatohexane (TTI) (with a purity of 90%). The resultant 1,3,6-triisocyanatohexane was subjected to distillation purification using a falling thin-film-type molecular distillation device (MS 300 type manufactured by SHIBATA SCIENTIFIC TECHNOLOGY LTD.) at a jacket temperature of 160° C. and at a pressure of 0.5 kPa to obtain 1,3,6-triisocyanatohexane. A methyl phenyl carbonate was added to the resultant such that the amount thereof, relative to isocyanate, became 13 ppm, to prepare an isocyanate composition. The amount of the 1,3,6-triisocyanatohexane in the composition, measured by GC, was 98.7% by mass, and the composition was a mixture composed of the 1,3,6-triisocyanatohexane and the methyl phenyl carbonate. APHA was 10.
Storage of Isocyanate Composition
300 g of the resultant isocyanate composition obtained above was put into a 500 mL storage container made of SUS, nitrogen exchange was performed, and the resultant was stored for 300 days in a storage environment in the Kojima area of Kurashiki City, Okayama Prefecture, Japan. After storage, the molecular weight of the resultant was analyzed by GPC, an area of the peak (referred to as peak 2) confirmed at a higher molecular weight side than the peak of 1,3,6-triisocyanatohexane (referred to as peak 1) was approximately 10%, relative to the peak 1. APHA was 20.

Example 2

Preparation of Isocyanate Composition
1,3,6-triisocyanatohexane was prepared in the same way as that of Example 1, and then a dibutyl phosphate was added thereto such that the amount the dibutyl phosphate, relative to isocyanate, became 7 ppm, to prepare an isocyanate composition. The amount of the 1,3,6-triisocyanatohexane in the composition, measured by GC, was 97% by mass, and APHA was 21.
Storage of Isocyanate Composition
The isocyanate composition prepared above was stored in the same way as that of Example 1. The result is shown in Table 1.

Synthesis Example B1

100 g (321 mmol) of a compound of the following formula (40) and 90.6 g (969 mmol) of phenol were reacted by heating the mixture under a nitrogen atmosphere at 100° C. When the reactant was analyzed by liquid chromatography to confirm the amount of the remaining phenol, the amount thereof was the detection limit or less. The reactant was used as a compound of the formula (1) or (33) in the present embodiment.

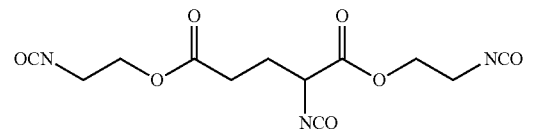

(40)

Example 3

Preparation of Isocyanate Composition
100 g of the compound of formula (40) and 9 g of the compound prepared in the Synthesis Example B1 were mixed to prepare an isocyanate composition. The amount of the compound of formula (1) or (33), relative to the isocyanate compound, was 90 ppm. Dimethyl carbonate and pentadecane were added thereto such that the amounts thereof, relative to the isocyanate compound, became 14 ppm and 1700 ppm, respectively, to prepare an isocyanate composition.
Storage of Isocyanate Composition
The isocyanate composition prepared above was stored in the same way as that of Example 1. The result is shown in Table 1.

Synthesis Example B2

100 g (495 mmol) of the compound of the following formula (44) and 73.4 g (990 mmol) of 1-butanol were reacted by heating the mixture under a nitrogen atmosphere at 100° C. When the reactant was analyzed by liquid chromatography to confirm the amount of the remaining butanol, the amount was the detection limit or less. The reactant was used as a compound of the formula (1) or (33) in the present embodiment.

(44)

Example 4

Preparation of Isocyanate Composition 55 g of the compound of the formula (44) and 1.5 mg of the compound obtained in the Synthesis Example B2 were mixed to prepare an isocyanate composition. The amount of the compound of formula (1) or (33), relative to the isocyanate compound, was 3 ppm.

Storage of Isocyanate Composition

The isocyanate composition prepared above was stored in the same way as that of Example 1. The result is shown in Table 1.

Synthesis Example B3

1,8-diisocyanato-4-isocyanatomethyloctane (hereinafter, may be referred to as TTI) was prepared in the same way as that of Example 1, except that 4-aminomethyloctane-1,8-diamine was used instead of 1,3,6-triaminohexane.

10.5 mg ($4.6 \times 10^{-2}$ mmol) of a titanium catalyst of the following formula (45) and TTI were reacted under a nitrogen atmosphere for 24 hours at 25° C. The obtained reactant was a compound having an UV absorption in an area of decamer or higher isocyanates in a measurement spectrum of gel permeation chromatography as shown in FIG. 1.

In FIG. 1, a horizontal axis indicates the retention time in the gel permeation chromatography, and the vertical axis indicates the absorption measured by the UV detector (at the wavelength of 254 nm). The retention time indicated asTTI decamer shows the retention time of the molecular weight corresponding to TTI decamer, and the retention time indicated as TTI shows the retention time of the molecular weight corresponding to TTI. The compound having an UV absorption in an area of decamer or higher isocyanates in a measurement spectrum of gel permeation chromatography obtained in Synthesis Example B3 was a compound having a peak at the retention time of 8.778 minutes of the gel permeation chromatography in FIG. 1.

(45)

Example 5

Preparation of Isocyanate Composition 500 g of TTI and 7.5 mg of a compound obtained in the Synthesis Example B3 were mixed to prepare an isocyanate composition. The amount of a compound having an UV absorption in an area of decamer or higher isocyanates, relative to the isocyanate compound, was 15 ppm.

Storage of Isocyanate Composition

The isocyanate composition prepared above was stored in the same way as that of Example 1. The result is shown in Table 1.

Example 6

Preparation of Isocyanate Composition

To a purified TTI liquid obtained in a similar manner to that of Example 1, a dibutyl phosphate and DURANATE (TLA-100 manufactured by Asahi Kasei Corporation), which was a mixture of uretdione and isocyanurate of hexamethylene diisocyanate, were added such that the respective amounts thereof, relative to the isocyanate compound, were 20 ppm.

Storage of Isocyanate Composition

The isocyanate composition prepared above was stored in the same way as that of Example 1. The result is shown in Table 1.

Examples 7-74, Comparative Examples 1-18

Isocyanates obtained in the same way as that of Example 1, except that the corresponding raw materials were used and the amounts of a "raw amine" and a stabilizer were changed as described in tables, were used. After the isocyanates were purified by any of the purification examples A1 to A3, isocyanate compositions were prepared using the isocyanates, and stored in the same way as that of Example 1. The results are shown in the following tables. In Comparative Examples 1, 3, 5, 7, 9, 11, 13, 15, and 17, gel generated in the isocyanate after the storage, and therefore GPC measurement could not be conducted.

In the following tables, the term "raw amine" means an amine used as a raw material to synthesize an isocyanate. For example, the case where a compound obtained by reaction of isocyanate and phenol was used as a compound of formula (1) or (33) as in the Synthesis Example B1 was indicated as "reactant of isocyanate and phenol". In the synthesis of the compound corresponding to the compound of formula (1) or (33), an isocyanate contained in the isocyanate composition was used, and two equivalents of a hydroxyl compound (aromatic hydroxy compound or alcohol), relative to isocyanate groups of the isocyanate, was used. As a "compound having an UV absorption in an area of decamer or higher isocyanates", a compound synthesized in a similar manner to that of the Synthesis Example B2 except that an isocyanate contained in the isocyanate composition was used instead of 1,3,6-triisocyanatohexane was used. As a compound having an isocyanurate group and/or a biuret group, DURANATE TPA-100, TKA-100, and TLA-100, manufactured by Asahi Kasei Corporation, were used.

In the following tables, the amount of a compound contained in the composition represents an amount, relative to an isocyanate compound.

TABLE 1

| | Raw amine | Isocyanate Structure | Isocyanate Amount (% by mass) | Compound contained in composition Compound | Amount (ppm by mass) | Before storage APHA | After storage for 300 days Area (%) of peak 2, relative to peak 1, by GPC measurement | APHA |
|---|---|---|---|---|---|---|---|---|
| Example 1 | H$_2$N–⋯–NH$_2$ with NH$_2$ | OCN–⋯–NCO with NCO | 99 | phenyl methyl carbonate (PhO–C(O)–O–CH$_3$) | 13 | 10 | 10 | 20 |
| Example 2 | H$_2$N–⋯–NH$_2$ with NH$_2$ | OCN–⋯–NCO with NCO | 97 | Dibutyl phosphate | 7 | 21 | 13 | 27 |
| Example 3 | HOOC–CH(NH$_2$)–⋯–COOH | OCN–CH$_2$–O–C(O)–C(NCO)–C(O)–O–CH$_2$–NCO | 97.4 | dimethyl carbonate | 14 | 15 | 3 | 21 |
| | HO–⋯–NH$_2$ | | | Reactant of isocyanate and phenol | 90 | | | |
| | | | | Pentadecane | 1700 | | | |
| Example 4 | 1,3,5-triaminobenzene (H$_2$N–C$_6$H$_3$(NH$_2$)$_2$) | 1,3,5-triisocyanatobenzene (OCN–C$_6$H$_3$(NCO)$_2$) | 97.5 | Reactant of isocyanate and 1-butanol | 3 | 16 | 7 | 27 |
| | | | | Chlorine | 82 | | | |
| | | | | Bromine | 2 | | | |
| Example 5 | H$_2$N–⋯–NH$_2$ with CH$_2$NH$_2$ branch | OCN–⋯–NCO with CH$_2$NCO branch | 97.5 | Compound having UV absorption at an area of decamere or higher isocyanate | 15 | 15 | 11 | 23 |
| Example 6 | H$_2$N–⋯–NH$_2$ with NH$_2$ | OCN–⋯–NCO with NCO | 97.5 | Dibutyl phosphate | 20 | 15 | 3 | 20 |
| | | | | DURANATE TLA-100 (manufactured by Asahi Kasei Corporation) | 20 | | | |

TABLE 2

| | Raw amine | Isocyanate Structure | Isocyanate Amount (% by mass) | Compound contained in composition Compound | Amount (ppm by mass) | Before storage APHA | After storage for 300 days Area (%) of peak 2, relative to peak 1, by GPC measurement | APHA |
|---|---|---|---|---|---|---|---|---|
| Example 7 | H$_2$N–⋯–CH(NH$_2$)–⋯–NH$_2$ | OCN–⋯–CH(NCO)–⋯–NCO | 98.9 | dipropyl carbonate (PrO–C(O)–OPr) | 660 | 10 | 3 | 18 |
| | | | | Dibenzyltoluene | 30 | | | |
| Example 8 | H$_2$N–⋯–NH$_2$ with NH$_2$ | OCN–⋯–NCO with NCO | 98.5 | phenyl methyl carbonate (PhO–C(O)–O–CH$_3$) | 970 | 26 | 9 | 33 |
| Example 9 | H$_2$N–⋯–NH$_2$ with NH$_2$ | OCN–⋯–NCO with NCO | 99 | Dibutyl phosphate | 90 | 18 | 2 | 27 |

TABLE 2-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Example 10 | 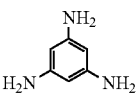 | 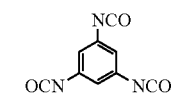 | 97.5 | Reactant of isocyanate and 1-butanol<br>Sulfuric acid | 15<br><br>15 | 10 | 6 | 20 |
| Example 11 | 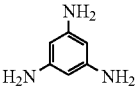 | 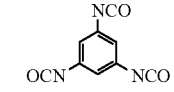 | 96 | Di-2-ethylhexyl phthalate | 960 | 16 | 12 | 25 |
| Example 12 | 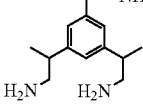 | 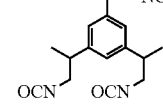 | 97 | 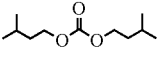 | 320 | 20 | 7 | 30 |
| | | | | Reactant of isocyanate and 3-methyl-1-butanol | 400 | | | |

TABLE 3

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Example 13 | 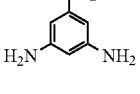 | 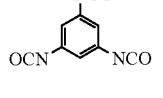 | 98.5 | Reactant of isocyanate and 1-butanol | 4500 | 20 | 10 | 45 |
| Example 14 | 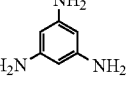 | 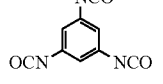 | 96 | Benzyltoluene<br>Isodecyl Phosphate | 28<br>20 | 16 | 10 | 25 |
| Example 15 | 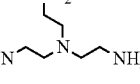 | 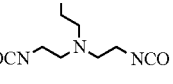 | 98.7 | Hexadecane | 2100 | 20 | 8 | 40 |
| Example 16 | 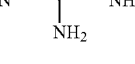 | 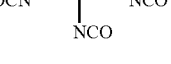 | 99.6 | 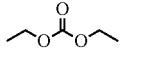<br><br>2,4,4-Trimethylpentene | 45<br><br>50 | 20 | 10 | 25 |

TABLE 3-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Example 17 | H₂N–CH₂CH₂–N(CH₂CH₂NH₂)–CH₂CH₂–NH₂ (triamine with central N) | OCN–CH₂CH₂–N(CH₂CH₂NCO)–CH₂CH₂–NCO | 98.7 | diethyl carbonate (EtO–C(=O)–OEt) | 90 | 20 | 2 | 25 |
| | | | | 1-Octene | 360 | | | |
| | | | | Hexadecane | 2100 | | | |
| Example 18 | H₂N–CH₂–CH(CH₂NH₂)–(CH₂)₃–NH₂ (branched triamine) | OCN–CH₂–CH(CH₂NCO)–(CH₂)₃–NCO | 97.1 | diphenyl carbonate (PhO–C(=O)–OPh) | 330 | 23 | 3 | 27 |
| | | | | Reactant of isocyanate and 4-cumylphenol | 530 | | | |
| | | | | | 25 | | | |

TABLE 4

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Example 19 | H₂N–CH₂–CH(NH₂)–(CH₂)₃–NH₂ (branched triamine) | OCN–CH₂–CH(NCO)–(CH₂)₃–NCO | 97.5 | phenyl methyl carbonate (PhO–C(=O)–OCH₃) | 9300 | 15 | 9 | 50 |
| Example 20 | H₂N–CH₂–C(CH₂NH₂)(...)–(CH₂)₃–NH₂ (branched triamine) | OCN–CH₂–C(CH₂NCO)(...)–(CH₂)₃–NCO | 97.9 | dibutyl carbonate (BuO–C(=O)–OBu) | 600 | 30 | 1 | 35 |
| | | | | 2-Methylbutene | 1100 | | | |
| | | | | Reactant of isocyanate and 4-tert-octylphenol | 20 | | | |
| | | | | Octadecane | 95 | | | |
| Example 21 | H₂N–CH₂–CH(CH₂NH₂)–(CH₂)₃–NH₂ (branched triamine) | OCN–CH₂–CH(CH₂NCO)–(CH₂)₃–NCO | 99 | diphenyl carbonate (PhO–C(=O)–OPh) | 238 | 22 | 4 | 23 |
| | | | | Diisodecyl adipate | 129 | | | |

TABLE 5

| | | Isocyanate | | Compound contained in composition | | Before storage APHA | After storage for 300 days | |
|---|---|---|---|---|---|---|---|---|
| | Raw amine | Structure | Amount (% by mass) | Compound | Amount (ppm by mass) | | Area (%) of peak 2, relative to peak 1, by GPC measurement | APHA |
| Example 22 | ornithine (H₂N-(CH₂)₃-CH(NH₂)-COOH) + HO-CH₂CH₂-NH₂ | OCN-(CH₂)₃-CH(NCO)-C(O)O-CH₂CH₂-NCO | 98.6 | diphenyl carbonate | 330 | 30 | 2 | 30 |
| | | | | Benzyltoluene | 260 | | | |
| | | | | Dibutyl phosphate | 50 | | | |
| Example 23 | H₂N-(CH₂)₂-CH(NH₂)-COOH + HO-CH₂CH₂-NH₂ | OCN-(CH₂)₂-CH(NCO)-C(O)O-CH₂CH₂-NCO | 98.5 | methyl phenyl carbonate | 50 | 18 | 2 | 26 |
| | | | | Styrene | 120 | | | |
| | | | | Reactant of isocyanate and 4-phenoxyphenol | 40 | | | |
| | | | | Diphenylether | 830 | | | |
| Example 24 | HOOC-CH(NH₂)-COOH + HO-CH₂CH₂-NH₂ | OCN-CH₂CH₂-O-C(O)-CH(NCO)-C(O)-O-CH₂CH₂-NCO | 98.4 | Compound having UV absorption at an area of decamere or higher isocyanate | 500 | 25 | 5 | 35 |
| | | | | Xylene | 800 | | | |
| | | | | Benzyl butyl phthalate | 400 | | | |

TABLE 6

| | | Isocyanate | | Compound contained in composition | | Before storage APHA | After storage for 300 days | |
|---|---|---|---|---|---|---|---|---|
| | Raw amine | Structure | Amount (% by mass) | Compound | Amount (ppm by mass) | | Area (%) of peak 2, relative to peak 1, by GPC measurement | APHA |
| Example 25 | HOOC-CH(NH₂)-CH₂-COOH + HO-CH₂CH₂-NH₂ | OCN-CH₂CH₂-O-C(O)-CH(NCO)-CH₂-C(O)-O-CH₂CH₂-NCO | 99.8 | dimethyl carbonate | 690 | 17 | 2 | 24 |
| | | | | α-Methylstyrene | 150 | | | |
| | | | | Ethylbenzene | 2000 | | | |
| | | | | Decamethyl-tetrasiloxane | 1400 | | | |
| Example 26 | 1,3,5-triaminobenzene | 1,3,5-triisocyanatobenzene | 97.2 | diethyl carbonate | 740 | 13 | 1 | 21 |

TABLE 6-continued

| | Isocyanate | | Compound contained in composition | | Before storage APHA | After storage for 300 days | |
|---|---|---|---|---|---|---|---|
| Raw amine | Structure | Amount (% by mass) | Compound | Amount (ppm by mass) | | Area (%) of peak 2, relative to peak 1, by GPC measurement | APHA |
| | | | Reactant of isocyanate and ethanol | 270 | | | |
| | | | Dichlorobenzene | 50 | | | |
| Example 27 | 2,4,6-triaminotoluene (NH$_2$, H$_2$N, NH$_2$ on methylbenzene) | 97.8 | diethyl carbonate (O=C(OEt)$_2$) | 80 | 24 | 2 | 30 |
| | | | Dimethyl sulfide | 170 | | | |
| Example 28 | 2,4-diamino-toluene derivative (NH$_2$, H$_2$N, NH$_2$) | 98 | Reactant of isocyanate and phenol | 120 | 19 | 0.5 | 26 |
| | | | Dilauryl phosphate | 25 | | | |

TABLE 7

| | Isocyanate | | Compound contained in composition | | Before storage APHA | After storage for 300 days | |
|---|---|---|---|---|---|---|---|
| Raw amine | Structure | Amount (% by mass) | Compound | Amount (ppm by mass) | | Area (%) of peak 2, relative to peak 1, by GPC measurement | APHA |
| Example 29 | 2,4,6-tris(aminomethyl)toluene | triisocyanatomethyl toluene structure | 97.8 | Reactant of isocyanate and cyclohexanol | 8600 | 30 | 3 | 38 |
| | | | Decyl ether | 800 | | | |
| Example 30 | aspartic acid (HOOC-CH(NH$_2$)-CH$_2$-COOH) and ethanolamine (HO-CH$_2$CH$_2$-NH$_2$) | OCN-CH$_2$CH$_2$-O-CO-CH(NCO)-CH$_2$-CO-O-CH$_2$CH$_2$-NCO | 99 | Xylene | 3 | 20 | 7 | 30 |
| Example 31 | 1,3,5-tris(1-aminoethyl)-2-methylbenzene | 1,3,5-tris(1-isocyanatoethyl)-2-methylbenzene | 97.4 | Reactant of isocyanate and 4-tert-aminophenol | 2500 | 22 | 1 | 32 |
| | | | Anisole | 420 | | | |

TABLE 7-continued

| | Isocyanate | | | Compound contained in composition | | Before storage APHA | After storage for 300 days | |
|---|---|---|---|---|---|---|---|---|
| Raw amine | Structure | | Amount (% by mass) | Compound | Amount (ppm by mass) | | Area (%) of peak 2, relative to peak 1, by GPC measurement | APHA |
| Example 32 | 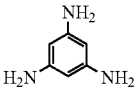 | 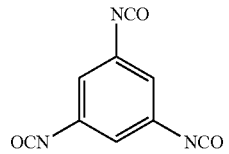 | 99 | Reactant of isocyanate and 4-tert-aminophenol | 500 | 30 | 7 | 40 |

TABLE 8

| | Isocyanate | | | Compound contained in composition | | Before storage APHA | After storage for 300 days | |
|---|---|---|---|---|---|---|---|---|
| Raw amine | Structure | | Amount (% by mass) | Compound | Amount (ppm by mass) | | Area (%) of peak 2, relative to peak 1, by GPC measurement | APHA |
| Example 33 | 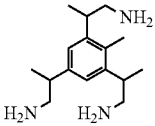 | 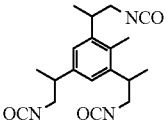 | 97.9 | Butyl phenyl ether | 30 | 28 | 1 | 37 |
| Example 34 | 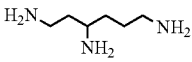 | 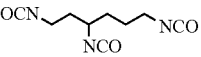 | 99.5 | Compound having UV absorption at an area of decamere or higher isocyanate | 2 | 20 | 17 | 55 |
| Example 35 | 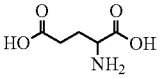 | 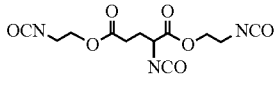 | 99.5 | Chlorine | 20 | 13 | 16 | 17 |
| Example 36 | 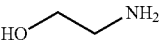 | 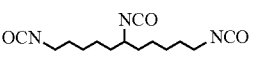 | 99.5 | Dibenzyl-toluene Chlorine | 30 41 | 19 | 8 | 32 |

TABLE 9

| | Raw amine | Isocyanate Structure | Isocyanate Amount (% by mass) | Compound contained in composition Compound | Compound contained in composition Amount (ppm by mass) | Before storage APHA | Area (%) of peak 2, relative to peak 1, by GPC measurement (After storage for 300 days) | APHA (After storage for 300 days) |
|---|---|---|---|---|---|---|---|---|
| Example 37 | 1,3,5-triaminobenzene (H2N, NH2, NH2 on benzene) | 1,3,5-triisocyanatobenzene (OCN, NCO, NCO on benzene) | 98.7 | Diethyl carbonate | 30 | 26 | 4 | 32 |
| | | | | 2,4,4-Trimethylpentene | 330 | | | |
| | | | | Chlorine | 67 | | | |
| Example 38 | H2N-CH(NH2)-CH2-NH2 (1,2,3-triaminopropane) | OCN-CH(NCO)-CH2-NCO | 98.1 | Phenyl methyl carbonate | 45 | 21 | 1 | 29 |
| | | | | Decamethyl-tetrasiloxane | 1400 | | | |
| | | | | Chlorine | 64 | | | |
| Example 39 | H2N-CH2CH2-N(CH2CH2-NH2)-CH2CH2-NH2 | OCN-CH2CH2-N(CH2CH2-NCO)-CH2CH2-NCO | 98.4 | 1-Octene | 360 | 26 | 3 | 34 |
| | | | | Hexadecane | 2100 | | | |
| | | | | Chlorine | 90 | | | |
| | | | | Bromine | 3 | | | |
| Example 40 | H2N-CH2CH2CH2-CH(CH2-NH2)-CH2CH2-NH2 | OCN-CH2CH2CH2-CH(CH2-NCO)-CH2CH2-NCO | 97.2 | Reactant of isocyanate and 4-tert-octylphenol | 20 | 12 | 4 | 21 |
| | | | | Decyl ether | 800 | | | |
| | | | | Chlorine | 84 | | | |

TABLE 10

| | Raw amine | Isocyanate Structure | Isocyanate Amount (% by mass) | Compound contained in composition Compound | Compound contained in composition Amount (ppm by mass) | Before storage APHA | Area (%) of peak 2, relative to peak 1, by GPC measurement (After storage for 300 days) | APHA (After storage for 300 days) |
|---|---|---|---|---|---|---|---|---|
| Example 41 | H2N-CH2-CH(CH2-NH2)-CH2CH2CH2-NH2 | OCN-CH2-CH(CH2-NCO)-CH2CH2CH2-NCO | 97.2 | Reactant of isocyanate and 4-tert-octylphenol | 8 | 12 | 2 | 17 |
| | | | | Diisopropyl phosphate | 8 | | | |
| Example 42 | H2N-CH2-CH(NH2)-CH2-CH(CH2-NH2)-CH2CH2-NH2 (branched tetraamine) | OCN-CH2-CH(NCO)-CH2-CH(CH2-NCO)-CH2CH2-NCO | 98.3 | Phenyl methyl carbonate | 600 | 21 | 4 | 27 |
| | | | | 2-Methylbutene | 1100 | | | |
| | | | | Octadecane | 95 | | | |
| | | | | Chlorine | 37 | | | |
| Example 43 | H2N-CH2CH2CH2-CH(NH2)-C(=O)-OH (ornithine); HO-CH2CH2-NH2 | OCN-CH2CH2CH2-CH(NCO)-C(=O)-O-CH2CH2-NCO | 98.3 | Benzyltoluene | 620 | 13 | 5 | 19 |
| | | | | Chlorine | 48 | | | |

TABLE 10-continued

| | Isocyanate | | Compound contained in composition | | Before storage APHA | After storage for 300 days | |
|---|---|---|---|---|---|---|---|
| Raw amine | Structure | Amount (% by mass) | Compound | Amount (ppm by mass) | | Area (%) of peak 2, relative to peak 1, by GPC measurement | APHA |
| Example 44 — H₂N-CH(NH₂)-(CH₂)-COOH; HO-CH₂CH₂-NH₂ | OCN-(CH₂)₂-C(NCO)(C(=O)O-CH₂CH₂-NCO) | 98.4 | Diphenyl carbonate | 50 | 25 | 3 | 26 |
| | | | Reactant of isocyanate and 4-phenoxyphenol | 40 | | | |
| | | | Styrene | 120 | | | |
| | | | Diphenylether | 930 | | | |
| | | | Chlorine | 77 | | | |

TABLE 11

| | Isocyanate | | Compound contained in composition | | Before storage APHA | After storage for 300 days | |
|---|---|---|---|---|---|---|---|
| Raw amine | Structure | Amount (% by mass) | Compound | Amount (ppm by mass) | | Area (%) of peak 2, relative to peak 1, by GPC measurement | APHA |
| Example 45 — HOOC-CH(NH₂)-CH₂-COOH; HO-CH₂CH₂-NH₂ | OCN-CH₂CH₂-O-C(=O)-CH(NCO)-C(=O)-O-CH₂CH₂-NCO | 98.1 | Dimethyl carbonate | 690 | 30 | 1 | 50 |
| | | | α-Methylstyrene | 150 | | | |
| | | | Ethylbenzene | 2000 | | | |
| | | | Chlorine | 23 | | | |
| Example 46 — 1,3,5-triaminobenzene | 1,3,5-triisocyanatobenzene | 98.2 | Reactant of isocyanate and ethanol | 270 | 24 | 4 | 29 |
| | | | Dimethyl sulfide | 170 | | | |
| | | | Chlorine | 38 | | | |
| Example 47 — 1,3,5-triaminobenzene | 1,3,5-triisocyanatobenzene | 96 | Di-2-ethylhexyl phosphate | 50 | 16 | 1 | 19 |
| | | | Diisodecyl phthalate | 70 | | | |
| Example 48 — 2-methyl-1,3,5-triaminobenzene | 2-methyl-1,3,5-triisocyanatobenzene | 98.2 | Reactant of isocyanate and cyclohexanol | 8600 | 20 | 1 | 45 |
| | | | Anisole | 420 | | | |
| | | | Chlorine | 57 | | | |

TABLE 12

| | Isocyanate | | | Compound contained in composition | | Before storage APHA | After storage for 300 days | |
|---|---|---|---|---|---|---|---|---|
| Raw amine | Structure | | Amount (% by mass) | Compound | Amount (ppm by mass) | | Area (%) of peak 2, relative to peak 1, by GPC measurement | APHA |
| Example 49 | 1,3,5-tris(aminomethyl)-2-methylbenzene | 1,3,5-tris(isocyanatomethyl)-2-methylbenzene | 98.7 | Butyl phenyl ether | 30 | 30 | 10 | 40 |
| | | | | Chlorine | 31 | | | |
| Example 50 | 1,3,5-tris(aminomethyl)-2-methylbenzene | 1,3,5-tris(isocyanatomethyl)-2-methylbenzene | 98.7 | DURANATE TPA-100 (manufactured by Asahi Kasei Corporation) | 9200 | 25 | 10 | 60 |
| Example 51 | 2,4-diaminobutanoic acid; ethanolamine | TKA-100-type triisocyanate | 98.4 | DURANATE TKA-100 (manufactured by Asahi Kasei Corporation) | 20 | 20 | 3 | 26 |
| Example 52 | aspartic acid; ethanolamine | bis(2-isocyanatoethyl) 2-isocyanatosuccinate | 98.7 | DURANATE TKA-100 (manufactured by Asahi Kasei Corporation) | 500 | 18 | 8 | 20 |
| | | | | Dilauryl phosphate | 50 | | | |

TABLE 13

| | Isocyanate | | | Compound contained in composition | | Before storage APHA | After storage for 300 days | |
|---|---|---|---|---|---|---|---|---|
| Raw amine | Structure | | Amount (% by mass) | Compound | Amount (ppm by mass) | | Area (%) of peak 2, relative to peak 1, by GPC measurement | APHA |
| Example 53 | 1,3,5-triaminobenzene | 1,3,5-triisocyanatobenzene | 96 | Di-2-ethylhexyl phthalate | 15 | 15 | 12 | 20 |
| Example 54 | aspartic acid; ethanolamine | bis(2-isocyanatoethyl) 2-isocyanatosuccinate | 98.7 | Compound having UV absorption at an area of decamere or higher isocyanate | 110 | 18 | 8 | 35 |
| | | | | Dimethyl carbonate | 1000 | | | |
| | | | | Benzyltoluene | 1000 | | | |
| | | | | 2-Isocyanatoacetate phenyl | 1000 | | | |

TABLE 13-continued

| | | Isocyanate | | Compound contained in composition | | Before storage APHA | After storage for 300 days | |
|---|---|---|---|---|---|---|---|---|
| | Raw amine | Structure | Amount (% by mass) | Compound | Amount (ppm by mass) | | Area (%) of peak 2, relative to peak 1, by GPC measurement | APHA |
| Example 55 | H₂N–⟨–NH₂ (with NH₂) | OCN–⟨–NCO (with NCO) | 97 | Phosphoric acid | 2 | 25 | 13 | 65 |
| Example 56 | H₂N–⟨–NH₂ (with NH₂) | OCN–⟨–NCO (with NCO) | 97.5 | Ph–O–C(O)–O–CH₃ | 1.5 | 20 | 9 | 53 |

TABLE 14

| | | Isocyanate | | Compound contained in composition | | Before storage APHA | After storage for 300 days | |
|---|---|---|---|---|---|---|---|---|
| | Raw amine | Structure | Amount (% by mass) | Compound | Amount (ppm by mass) | | Area (%) of peak 2, relative to peak 1, by GPC measurement | APHA |
| Example 57 | H₂N–⟨–NH₂ (with NH₂) | OCN–⟨–NCO (with NCO) | 97.5 | Compound having UV absorption at an area of decamere or higher isocyanate | 950 | 15 | 11 | 23 |
| Example 58 | H₂N–⟨–C(O)OH (with NH₂); HO–⟨–NH₂ | OCN–⟨–C(O)–O–⟨–NCO (with NCO) | 98.4 | DURANATE TKA-100 (manufactured by Asahi Kasei Corporation) | 890 | 20 | 3 | 26 |

TABLE 15

| | | Isocyanate | | Compound contained in composition | | Before storage APHA | After storage for 300 days | |
|---|---|---|---|---|---|---|---|---|
| | Raw amine | Structure | Amount (% by mass) | Compound | Amount (ppm by mass) | | Area (%) of peak 2, relative to peak 1, by GPC measurement. | APHA |
| Example 59 | trimethylbenzene with three CH₂NH₂ groups and methyl | trimethylbenzene with three CH₂NCO groups and methyl | 98.7 | DURANATE TPA-100 (manufactured by Asahi Kasei Corporation) | 1.5 | 30 | 10 | 75 |

TABLE 15-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement. | After storage for 300 days |
|---|---|---|---|---|---|---|---|---|
| Example 60 | 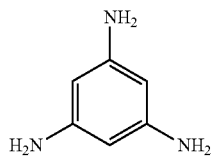 | 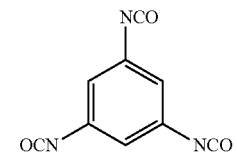 | 96 | Di-2-ethylhexyl phthalate | 8800 | 40 | 12 | 75 |
| Example 61 | 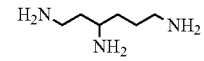 | 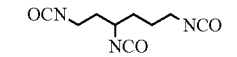 | 97 | Phosphoric acid | 1200 | 30 | 13 | 65 |
| Example 62 | 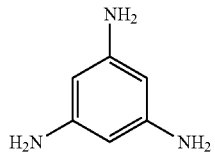 | 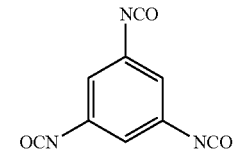 | 98.7 | Reactant of isocyanate and 1-butanol | 1.5 | 35 | 10 | 73 |

TABLE 16

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement. | After storage for 300 days |
|---|---|---|---|---|---|---|---|---|
| Example 63 |  | 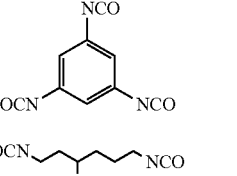 | 98.7 | Reactant of isocyanate and 1-butanol | 9500 | 35 | 10 | 80 |
| Example 64 | 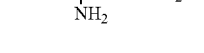 |  | 97 | Compound having UV absorption at an area of decamere or higher isocyanate | 110 | 18 | 8 | 35 |
| | | | | Diphenyl carbonate | 1000 | | | |
| | | | | Dibenzyltoluene | 1000 | | | |
| Example 65 | 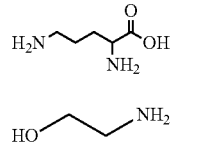 | 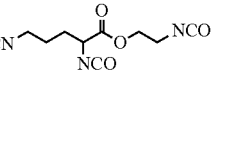 | 98.5 | DURANATE TKA-100 | 800 | 20 | 10 | 30 |
| | | | | Diphenyl carbonate | 800 | | | |
| | | | | Benzyltoluene | 800 | | | |
| | | | | Phenyl 2,6-diisocyanato-hexanoate | 800 | | | |
| | | | | Reactant of isocyanate and phenol | 500 | | | |
| | | | | Dibutyl phosphate | 50 | | | |

TABLE 17

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement. | |
|---|---|---|---|---|---|---|---|---|
| Example 66 | H₂N–CH(NH₂)–CH₂CH₂–NH₂ (triamine) | OCN–CH(NCO)–CH₂CH₂–NCO | 99.5 | Compound having UV absorption at an area of decamere or higher isocyanate | 9800 | 20 | 17 | 58 |
| Example 67 | 1,3,5-triaminobenzene | 1,3,5-triisocyanatobenzene | 98.7 | Reactant of isocyanate and 1-butanol / Phenyl 2-isocyanato-propanoate | 500 / 500 | 35 | 10 | 73 |
| Example 68 | 1,3,5-triaminobenzene | 1,3,5-triisocyanatobenzene | 96 | Di-2-ethylhexyl phthalate | 2 | 30 | 12 | 70 |
| Example 69 | H₂N–(CH₂)₅–NH₂ | OCN–(CH₂)₅–NCO | 98.3 | Compound having UV absorption at an area of decamere or higher isocyanate | 9000 | 10 | 3 | 10 |

TABLE 18

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement. | |
|---|---|---|---|---|---|---|---|---|
| Example 70 | H₂N–(CH₂)₆–NH₂ | OCN–(CH₂)₆–NCO | 98.3 | Compound having UV absorption at an area of decamere or higher isocyanate | 20 | 10 | 5 | 10 |
| Example 71 | Isophorone diamine | Isophorone diisocyanate | 98.3 | DURANATE TLA-100 (manufactured by Asahi Kasei Corporation) | 8000 | 10 | 5 | 10 |

TABLE 18-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement. | After storage for 300 days APHA |
|---|---|---|---|---|---|---|---|---|
| Example 72 | (trimethyl cyclohexane diamine: NH₂ and CH₂NH₂ substituents) | (corresponding diisocyanate: NCO and CH₂NCO) | 98.3 | DURANATE TLA-100 (manufactured by Asahi Kasei Corporation) | 20 | 10 | 10 | 10 |
| Example 73 | H₂N–(cyclohexyl)–CH₂–(cyclohexyl)–NH₂ | OCN–(cyclohexyl)–CH₂–(cyclohexyl)–NCO | 98.3 | Di-2-ethylhexyl phthalate | 8500 | 10 | 15 | 10 |

TABLE 19

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Example 74 | H₂N–(cyclohexyl)–CH₂–(cyclohexyl)–NH₂ | OCN–(cyclohexyl)–CH₂–(cyclohexyl)–NCO | 98.3 | Di-2-ethylhexyl phthalate | 20 | 10 | 10 | 10 |
| Comparative Example 1 | H₂N–CH₂–CH(NH₂)–CH₂–CH₂–NH₂ (triamine) | OCN–CH₂–CH(NCO)–CH₂–CH₂–NCO | 99.2 | phenyl methyl carbonate (PhO–C(=O)–O–CH₃) | 0.3 | 25 | Since gelatinous component generated, measurement could not be conducted. | 80 |
| Comparative Example 2 | H₂N–CH₂–CH(NH₂)–CH₂–CH₂–NH₂ | OCN–CH₂–CH(NCO)–CH₂–CH₂–NCO | 97.4 | phenyl methyl carbonate (PhO–C(=O)–O–CH₃) | 21000 | 19 | 20 | 150 |

TABLE 20

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Comparative Example 3 | 1,3,5-triaminobenzene (NH₂, NH₂, NH₂ on benzene) | 1,3,5-triisocyanatobenzene (NCO, NCO, NCO on benzene) | 99.3 | Reactant of isocyanate and 1-butanol | 0.8 | 21 | Since gelatinous component generated, measurement could not be conducted. | 100 |

TABLE 20-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Comparative Example 4 | 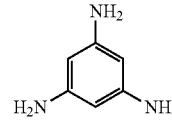 | 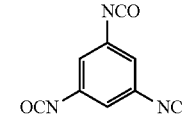 | 97.1 | Reactant of isocyanate and 1-butanol | 22000 | 11 | 18 | 200 |
| Comparative Example 5 | 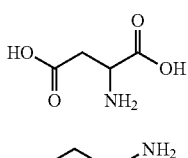 | 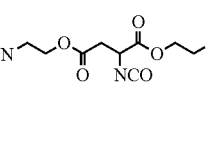 | 99.5 | Xylene | 0.5 | 30 | Since gelatinous component generated, measurement could not be conducted. | 90 |
| Comparative Example 6 | 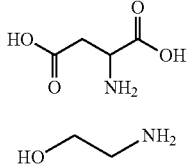 | 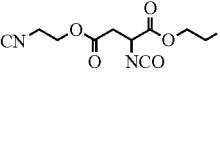 | 974 | Xylene | 22000 | 29 | 25 | 160 |

TABLE 21

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Comparative Example 7 | 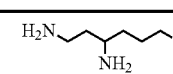 | 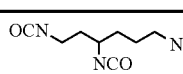 | 98.3 | Di-2-ethylhexyl phthalate | 0.5 | 19 | Since gelatinous component generated, measurement could not be conducted. | 80 |
| Comparative Example 8 | 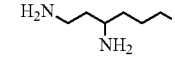 | 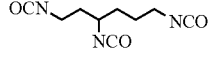 | 98.3 | Di-2-ethylhexyl phthalate | 12000 | 27 | 22 | 150 |
| Comparative Example 9 | 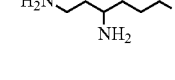 | 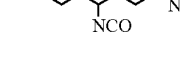 | 98.3 | Compound having UV absorption at an area of decamer or higher isocyanate | 15000 | 25 | Since gelatinous component generated, measurement could not be conducted. | 80 |
| Comparative Example 10 | 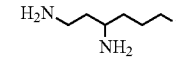 | 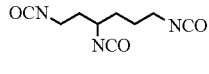 | 98.3 | Compound having UV absorption at an area of decamer or higher isocyanate | 0.5 | 15 | 22 | 140 |

TABLE 22

| | | Isocyanate | | Compound contained in composition | | After storage for 300 days | | |
|---|---|---|---|---|---|---|---|---|
| | | | | | | | Area (%) of peak 2, relative | |
| | Raw amine | Structure | Amount (% by mass) | Compound | Amount (ppm by mass) | Before storage APHA | to peak 1, by GPC measurement | APHA |
| Comparative Example 11 | 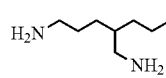 | 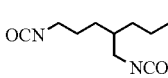 | 98.3 | DURANATE TKA-100 (manufactured by Asahi Kasei Corporation) | 12000 | 25 | Since gelatinous component generated, measurement could not be conducted. | 75 |
| Comparative Example 12 | 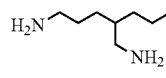 | 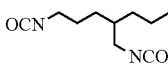 | 98.3 | DURANATE TKA-100 (manufactured by Asahi Kasei Corporation) | 0.5 | 15 | 22 | 130 |
| Comparative Example 13 | 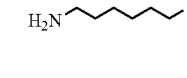 | 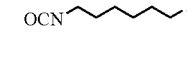 | 98.3 | Compound having UV absorption at an area of decamere or higher isocyanate | 11000 | 10 | Since gelatinous component generated, measurement could not be conducted. | 75 |
| Comparative Example 14 | 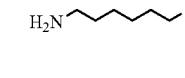 | 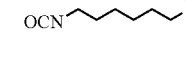 | 98.3 | Compound having UV absorption at an area of decamere or higher isocyanate | 0.3 | 10 | 22 | 130 |

TABLE 23

| | | Isocyanate | | Compound contained in composition | | After storage for 300 days | | |
|---|---|---|---|---|---|---|---|---|
| | | | | | | | Area (%) of peak 2, relative | |
| | Raw amine | Structure | Amount (% by mass) | Compound | Amount (ppm by mass) | Before storage APHA | to peak 1, by GPC measurement | APHA |
| Comparative Example 15 | 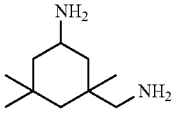 | 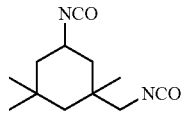 | 98.3 | DURANATE TLA-100 (manufactured by Asahi Kasei Corporation) | 13000 | 10 | Since gelatinous component generated, measurement could not be conducted. | 75 |
| Comparative Example 16 | 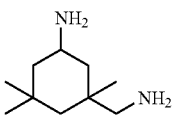 | 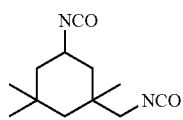 | 98.3 | DURANATE TLA-100 (manufactured by Asahi Kasei Corporation) | 0.2 | 10 | 22 | 130 |

TABLE 23-continued

| | Raw amine | Isocyanate Structure | Isocyanate Amount (% by mass) | Compound contained in composition Compound | Compound contained in composition Amount (ppm by mass) | Before storage APHA | After storage for 300 days Area (%) of peak 2, relative to peak 1, by GPC measurement | After storage for 300 days APHA |
|---|---|---|---|---|---|---|---|---|
| Comparative Example 17 | H₂N–⬡–⬡–NH₂ | OCN–⬡–⬡–NCO | 98.3 | Di-2-ethylhexyl phthalate | 10500 | 10 | Since gelatinous component generated, measurement could not be conducted. | 75 |
| Comparative Example 18 | H₂N–⬡–⬡–NH₂ | OCN–⬡–⬡–NCO | 98.3 | Di-2-ethylhexyl phthalate | 0.5 | 10 | 22 | 130 |

Example C1

Synthesis of Isocyanate Polymer 100 g of the isocyanate composition after storage in Example 1 was put into a four-necked flask made of glass and equipped with a thermometer, a stirrer and a nitrogen sealed tube, an air in the flask was replaced with nitrogen, and the composition was heated at 70° C. while conducting stirring. The refractive index of the reaction liquid was measured to gradually add a catalyst (tetramethylammoniumhydroxide) to the composition until the conversion rate of the isocyanate became 20%, and, when the conversion rate became 20%, 0.5 g of an 85% phosphoric acid aqueous solution was added thereto to terminate the reaction.

After the reaction, the reactant liquid was subjected to filtration, and unreacted isocyanates were removed at 160° C. (0.5 Pa) for the first time and at 180° C. (0.5 Pa) for the second time using a falling thin-film-type molecular distillation device to obtain an isocyanate polymer. As a result of FT-IR measurement and $^1$H NMR measurement of the resultant isocyanate polymer, it was confirmed that the resultant isocyanate polymer had an isocyanurate structure (structure of the formula (2) and an isocyanate terminal structure (structure of the formula (A) or (B)), and was an average isocyanate 3.5 mer. The conversion rate was determined by measuring the change in the refractive index of a reactant liquid as a sample at 30° C. using a refractometer (trade name of RA-520 manufactured by KYOTO ELECTRONICS MANUFACTURING CO., LTD).

Evaluation in Terms of Weather Resistance of Isocyanate Polymer

The isocyanurate polymer and the polyester polyol (manufactured by Nuplex Resin under the trade name of Setal 166) were formulated such that the equivalent ratio of isocyanate groups/hydroxy groups became 1.0, and then a mixture composed of ethyl acetate, toluene, butyl acetate, xylene, and propylene glycol monomethyl ether acetate (mass ratio of 30/30/20/15/5) was added thereto such that the mass of the solid content including the isocyanurate polymer and the polyol became 50% to obtain a coating material solution. The coating material solution was applied on a white enamel coated plate by conducting applicator coating such that the film thickness after drying became 40 jim, and then the coated film was cured at a temperature of 20° C. and at a humidity of 63% for 1 week, followed by evaluating the weather resistance of the coated plate. The weather resistance was evaluated using a dew panel weather meter (manufactured by Suga Test Instruments Co., Ltd.). The evaluation was performed in accordance with JIS D 0205 under the conditions in which the irradiance was 30 W/m², the panel temperature was 60° C., and the irradiation time and the condensation time were repeated at a cycle operation every 4 hours.

When the exposure time reached 1200 hours, the gloss retention rate of the coated plate was 80% or more.

Example D1

An internal portion of a four-necked flask equipped with a stirrer, a thermometer, a cooling tube, and a FT-IR probe (manufactured by METTLER TOLEDO, React-IR, AgX probe) was replaced with nitrogen, 120 g of the isocyanate composition after storage in Example 2 and 130 g of polyester polyol "PLACCEL 305" (trade name manufactured by DAICEL CORPORATION) derived from travalent alcohol and ε-caprolactone were put therein, and then the mixture was heated at 130° C. while stirring the mixture. The reaction was progressing while the amount of produced urethane groups by FT-IR was confirmed.

Then, 0.5 g of an octanol solution containing 20% zirconyl 2-ethylhexanoate was added to the resultant to allow an allophanate-forming reaction to proceed. When the increase in the refractive index became 0.0051, a 2-ethyl-1-hexanol solution containing a pyrophosphoric acid at a solid content of 10% (the trade name "phosphoric acid (105%)" manufactured by Taihei Chemical Industrial Co., Ltd., wad diluted with 2-ethyl-1-hexanol) was added to the resultant to stop the reaction.

After the reaction liquid was filtrated, distillation was conducted at 180° C. and 0.3 kPa using a falling thin-film evaporator to collect the residue. The residue was further subjected to distillation using a thin film distillation apparatus at 160° C. and 0.3 kPa to obtain an isocyanate polymer.

The resultant isocyanate polymer was used to evaluate in terms of the weather resistance of the isocyanate polymer in a similar manner to that of Example C1. When the exposure time reached 1200 hours, the gloss retention rate was 80% or more.

Example E1

400 g of TTI and 200 g of the composition in Example 1 was weighed in a four-necked flask made of glass and equipped with a thermometer, a stirrer and a nitrogen sealed tube, nitrogen replacement was conducted in the reactor, and then the mixture was heated at 65° C. Then, 140 g of 2-ethylhexanol was added to the resultant, and then the mixture was stirred for 10 minutes. Then, 50 g of a 5% isobutanol solution of tetrabutylammonium acetate was added to the resultant over 60 minutes. The temperature was maintained at 65±2° C. during the reaction. 5 g of an 85% phosphoric acid aqueous solution was added thereto as a reaction terminating agent, the mixture was heated to 100° C., and then stirred for 1 hour after the temperature reached 100° C. The reaction liquid was colorless and transparent. The reaction liquid was filtrated with a membrane filter having a fine pore size of 1 μm to separate a reaction residue, and then an unreacted TTI was distilled away with a thin film distillation apparatus to obtain a polyisocyanate composition. The resultant polyisocyanate composition was approximately colorless and transparent.

As a result of FT-IR measurement and $^1$H NMR of the resultant isocyanate polymer, it was confirmed that the resultant isocyanate polymer had an isocyanurate structure (structure of the formula (2)), an allophanate structure (structure of the formula (6)), a urethane group (structure of the formula (8) in which $R^4$ represented 2-ethylhexyl group), and an isocyanate terminal structure (structure of the formula (A) and (B)), and was an isocyanate 3.3mer.

INDUSTRIAL APPLICABILITY

According to the present invention, an isocyanate composition containing a difunctional diisocyanate and/or trifunctional or more-functional isocyanate, the storage stability of which is improved, is provided. In addition, according to the present invention, a method for producing a polyisocyanate composition by polymerizing the isocyanate composition is provided.

The invention claimed is:
1. An isocyanate composition comprising:
a trifunctional or more-functional isocyanate compound; and
1.0 ppm by mass to $1.0 \times 10^4$ ppm, based on the isocyanate compound, of a compound having at least one unsaturated bond excluding unsaturated bonds constituting an aromatic ring, the compound being different from the isocyanate compound,
wherein the compound having at least one unsaturated bond is a compound having an UV absorption in a region that decamer or higher isocyanates elute in a measurement spectrum of gel permeation chromatography, and
the compound having an UV absorption in a region that decamer or higher isocyanates elute in a measurement spectrum of gel permeation chromatography is a polymer derived from the trifunctional or more-functional isocyanate compound.
2. The isocyanate composition according to claim 1, further comprising, based on the isocyanate compound,
1.0 ppm by mass to $1.0 \times 10^4$ ppm by mass of at least one inert compound selected from the group consisting of hydrocarbon compounds, ether compounds, sulfide compounds, halogenated hydrocarbon compounds, silicon-containing hydrocarbon compounds, silicon-containing ether compounds and silicon-containing sulfide compounds, the inert compound being free from unsaturated bonds between carbon atoms and unsaturated bonds between a carbon atom and an oxygen atom, excluding unsaturated bonds constituting an aromatic ring, and/or,
1.0 ppm by mass to $1.0 \times 10^3$ ppm by mass of a sulfuric acid and/or a sulfuric acid ester, and/or,
1.0 ppm by mass to $1.0 \times 10^3$ ppm by mass of a phosphoric acid and/or a phosphoric acid ester.
3. The isocyanate composition according to claim 1, further comprising 1.0 ppm by mass to $1.0 \times 10^2$ ppm by mass, based on the isocyanate compound, of a halogen atom which is not derived from a halogenated hydrocarbon compound.
4. The isocyanate composition according to claim 1, wherein an amount of the isocyanate compound is 97% by mass or more, based on a total of the isocyanate composition.
5. A method for producing an isocyanate polymer, comprising reacting an isocyanate compound comprised in an isocyanate composition of claim 1,
wherein the isocyanate polymer comprises: a unit of formula (A) or (B); and at least one unit selected from the group consisting of units of formulae (2), (3), (4), (5), (6), (7) and (8), and
a nitrogen atom constituting the isocyanate polymer bonds with a carbon atom:

(A)

(B)

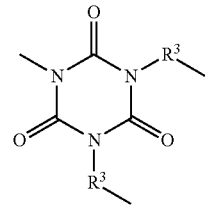

(2)

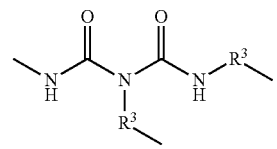

(3)

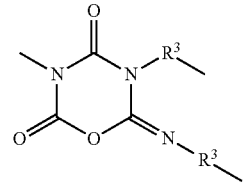

(4)

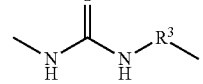

(5)

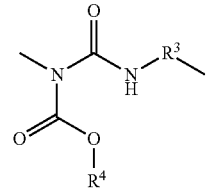

(6)

-continued

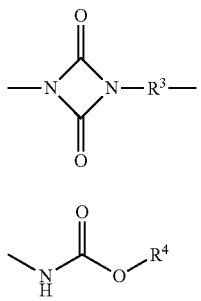
(7)

—NH—C(=O)—O—R⁴
(8)

wherein, each $R^3$ independently represents a residual group obtained by removing two isocyanate groups from the isocyanate compound, and each $R^4$ independently represents a monovalent organic group.

6. The isocyanate composition according to claim 1, wherein the compound having an UV absorption in a region that decamer or higher isocyanates elute in a measurement spectrum of gel permeation chromatography has a 1-nylon body structure of formula (37):

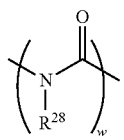
(37)

wherein $R^{29}$ is a group obtained by removing one isocyanate group from the trifunctional or more-functional isocyanate compound, and w represents an integer of 1 or more.

* * * * *